US009491378B2

United States Patent
Kane et al.

(10) Patent No.: US 9,491,378 B2
(45) Date of Patent: Nov. 8, 2016

(54) METHODS AND SYSTEMS FOR DETECTION AND IDENTIFICATION OF CONCEALED MATERIALS

(71) Applicants: James A. Kane, Needham Heights, MA (US); Ranganathan Shashidhar, Needham Heights, MA (US)

(72) Inventors: James A. Kane, Needham Heights, MA (US); Ranganathan Shashidhar, Needham Heights, MA (US)

(73) Assignee: Polestar Technologies, Inc., Needham Heights, MA (US)

(*) Notice: Subject to any disclaimer, the term of this patent is extended or adjusted under 35 U.S.C. 154(b) by 132 days.

(21) Appl. No.: 14/246,606

(22) Filed: Apr. 7, 2014

(65) Prior Publication Data

US 2015/0288893 A1    Oct. 8, 2015

(51) Int. Cl.
| | |
|---|---|
| *H04N 5/33* | (2006.01) |
| *H04N 5/225* | (2006.01) |
| *G01J 3/10* | (2006.01) |
| *G01J 3/28* | (2006.01) |
| *G01J 3/32* | (2006.01) |
| *G01J 3/42* | (2006.01) |
| *G01J 3/433* | (2006.01) |
| *G01J 3/02* | (2006.01) |
| *G01N 21/31* | (2006.01) |
| *G02B 27/10* | (2006.01) |
| *G01N 21/84* | (2006.01) |

(52) U.S. Cl.
CPC ............. *H04N 5/332* (2013.01); *G01J 3/0218* (2013.01); *G01J 3/0272* (2013.01); *G01J 3/10* (2013.01); *G01J 3/2803* (2013.01); *G01J 3/32* (2013.01); *G01J 3/42* (2013.01); *G01J 3/433* (2013.01); *G01N 21/314* (2013.01); *H04N 5/2256* (2013.01); *G01N 21/8422* (2013.01); *G01N 2201/0221* (2013.01); *G02B 27/1013* (2013.01)

(58) Field of Classification Search
CPC ..................................................... H04N 5/332
USPC .......................................................... 348/164
See application file for complete search history.

(56) References Cited

U.S. PATENT DOCUMENTS

| 8,547,274 B2 * | 10/2013 | Reinpoldt, III | ....... G01S 13/887 |
| | | | 342/179 |
| 2013/0050007 A1 * | 2/2013 | Ammar | .................. G01S 7/412 |
| | | | 342/22 |

* cited by examiner

*Primary Examiner* — Richard Torrente

(74) *Attorney, Agent, or Firm* — Burns & Levinson LLP; Orlando Lopez

(57) ABSTRACT

Methods and systems for efficiently and accurately detecting and identifying concealed materials. The system includes an analysis subsystem configured to process a number of pixelated images, the number of pixelated images obtained by repeatedly illuminating, through a patterning component, regions, where an electromagnetic radiation source, from a number of electromagnetic radiation sources, illuminates the patterning component, each repetition performed with a different wavelength. A number of Global pixelated images are obtained. The number of global pixelated images, after processing, constitute a vector of processed data at each pixel from a number of pixels. At each pixel, the vector of processed data is compared to a predetermined vector corresponding to a predetermined material, presence of the predetermined material being determined by the comparison.

16 Claims, 21 Drawing Sheets

```
┌─────────────────────────────────────────────┐
│ SEQUENTIALLY ILLUMINATING, THROUGH A        │
│ PATTERNING COMPONENT FOR A NUMBER OF        │
│ EXPOSURES, AN AREA OF INTEREST WITH         │
│ ELECTROMAGNETIC RADIATION; EACH             │
│ EXPOSURE COMPRISING ELECTROMAGNETIC         │
│ RADIATION AT SUBSTANTIALLY ONE              │
│ WAVELENGTHS FROM A NUMBER OF                │
│ WAVELENGTHS                                 │
│                   210                       │
└─────────────────────────────────────────────┘
                      ↓
┌─────────────────────────────────────────────┐
│ DETECTING, AT A NUMBER OF PIXELS, AND AT    │
│ EACH EXPOSURE, REFLECTED/SCATTERED          │
│ ELECTROMAGNETIC RADIATION FROM THE          │
│ AREA OF INTEREST; THE REFLECTED/SCATTERED   │
│ ELECTROMAGNETIC RADIATION FROM THE AREA     │
│ OF INTEREST BEING DETECTED BY ONE OR        │
│ MORE DETECTING COMPONENTS                   │
│                   220                       │
└─────────────────────────────────────────────┘
                      ↓
┌─────────────────────────────────────────────┐
│ OBTAINING A NUMBER OF PIXELATED IMAGES,     │
│ ONE OR MORE AT EACH WAVELENGTH, FROM        │
│ THE ONE OR MORE DETECTING COMPONENTS;       │
│ ILLUMINATION THROUGH THE PATTERNING         │
│ COMPONENT PRODUCING AREAS IN EACH           │
│ PIXELATED IMAGE THAT ARE NOT DIRECTLY       │
│ ILLUMINATED                                 │
│                   225                       │
└─────────────────────────────────────────────┘
                      ↓
┌─────────────────────────────────────────────┐
│ OBTAINING, FOR EACH ONE OR MORE PIXELATED   │
│ IMAGES FROM THE NUMBER OF PIXELATED         │
│ IMAGES, ONE GLOBAL PIXELATED IMAGE,         │
│ PRODUCED SUBSTANTIALLY BY THE AREAS ARE     │
│ NOT DIRECTLY ILLUMINATED                    │
│                   227                       │
└─────────────────────────────────────────────┘
                      ↓
┌─────────────────────────────────────────────┐
│ PROCESSING A NUMBER OF GLOBAL PIXELATED     │
│ IMAGES, THE NUMBER OF GLOBAL PIXELATED      │
│ IMAGES, AFTER PROCESSING, CONSTITUTING A    │
│ VECTOR OF PROCESSED DATA AT EACH PIXEL      │
│ FROM A NUMBER OF PIXELS                     │
│                   230                       │
└─────────────────────────────────────────────┘
                      ↓
┌─────────────────────────────────────────────┐
│ COMPARING, AT EACH PIXEL, THE VECTOR OF     │
│ PROCESSED DATA TO A PREDETERMINED VECTOR    │
│ CORRESPONDING TO A PREDETERMINED MATERIAL   │
│                   240                       │
└─────────────────────────────────────────────┘
```

Fig. 7a

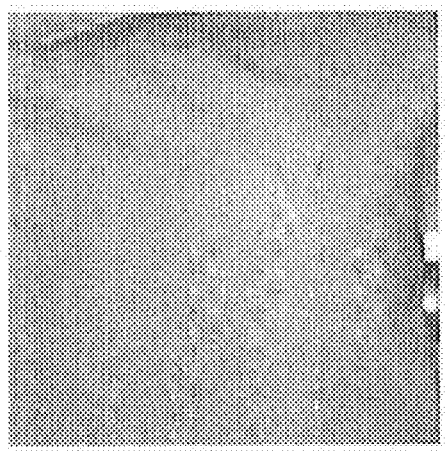 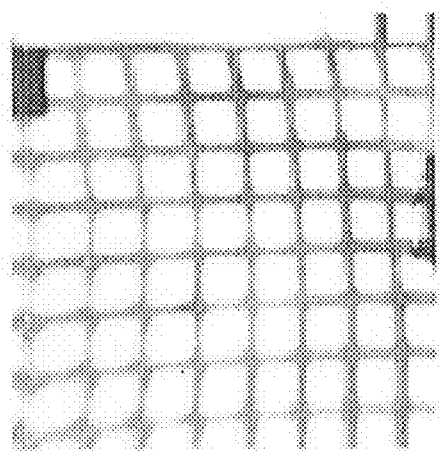
Fig. 12a                    Fig. 12b

METHODS AND SYSTEMS FOR DETECTION AND IDENTIFICATION OF CONCEALED MATERIALS

STATEMENT REGARDING FEDERALLY SPONSORED RESEARCH OR DEVELOPMENT

This invention was made partially with U.S. Government support from the U.S. Army under contract W31P4Q-09-C-0585. The U.S. Government may have certain rights in the invention.

BACKGROUND

These teachings relate generally to methods and systems for detecting concealed materials.

Numerous conventional approaches have been taken in the field of standoff detection and identification to attempt to detect and identify materials, especially explosives, drugs, etc., concealed under clothing. Such conventional approaches that have been reported in the literature for standoff detection and identification of concealed contraband materials include x-ray backscatter imaging, neutron excited gamma ray emission spectroscopy, terahertz reflection spectroscopy, and laser induced breakdown spectroscopy.

Problems with the x-ray backscattering imaging approach include poor chemical selectivity for chemical identification with high potential for false positives, large size and weight of instrumentation which prevents the system from being man-portable, and human health risk from x-ray exposure.

Problems with neutron excited gamma ray spectroscopy include: limited chemical selectivity resulting from the measurement only producing elemental concentration results, limited sensitivity, and long measurement times at significant standoff distances (i.e. 1 ft. or greater), and substantial human health risks. Measurements providing only elemental analysis information would not be likely to be able to identify explosive materials such as triacetaonetriperoxide that contain only the elements C, H, and O, and identification of drugs would be very difficult.

Problems with terahertz spectroscopy include: slow measurement time, as well as substantial problems with interference from absorption of terahertz radiation by atmospheric water vapor for standoff distances greater than 10 ft. In addition, the size and weight of the equipment are too great for man-portability.

Laser induced breakdown spectroscopy (LIBS) is a trace detection method that can detect and identify small particles of explosive or other materials on the outside of a surface in a standoff mode. The primary problem with LIES is that it cannot detect or identify materials concealed underneath a covering layer such as cloth and can only detect explosive particles on the outside surface of clothing. Explosives or other contraband materials that are well sealed in a plastic bag and concealed under clothing, where the outside surface of the clothing was not contaminated with the dust of the contraband material, could not be detected or identified with LIES.

Further, NIR spectroscopy has been used to identify chemical compounds. In particular, Li, et al. disclose a method of analyzing NIR data, so as to identify various solid forms of chemical compounds and drug candidates. This method includes the steps of: (1) computing the second derivative spectra for collected NIR spectra; (2) applying principal component analysis (PCA) of the second derivative spectra at predetermined wavelengths either the entire wavelength region or a selected wavelength region for segregating the samples; identifying the groups and group membership from the PCA graph, and further evaluating group members by calculating Mahalanobis distances of a given group to assess qualification of the group members. However, this method is merely an initial exploratory analysis of near-infrared spectra designed to identify how many different components or materials are present in an unknown sample, and how different their spectra are.

Additional conventional methods include using NIR spectroscopy to attempt to identify components relative to a saved calibration library, via identification of absorption wavelengths, and comparison thereof to known standards. For example, an explosive device detection method and system based on differential emissivity have been disclosed. This method and system monitors the emissivity levels of target subjects in monitored zones by repeatedly scanning the pixels of an infrared photodetector array, and then processing the pixel values to determine if they correspond to at least one calibrated emissivity level associated with a concealed explosive device. The calibration techniques of that method involve attempts to eliminate the effects of clothing and other personal items, as well as environmental factors, but suffer from a concentration mainly on differences in emissivity levels caused by distance of the target from the source (IR photodetector), rather than increasing the contrast/difference in measured emissivity between the covering materials and the concealed contraband materials.

Further, such conventional methods are inaccurate, when used to attempt to identify materials concealed under clothing, covering materials, etc., due to the difficulties inherent in filtering out the wavelengths reflected from the clothing, covering materials, containment materials, etc., as well as, importantly, ambient light, sunlight, etc, Thus, to obtain accurate measurements, such conventional NIR methods generally are confined to laboratory or laboratory-like environments, not public areas, such as airports.

In view of the above, there is a need for providing a method to efficiently and accurately detect and identify concealed materials, such as explosives, drugs, or hazardous materials, concealed on a person under clothing or in a backpack, or concealed in unattended paper, plastic, cloth or leather bags (including backpacks), and a system for carrying out same.

BRIEF SUMMARY

Methods and systems for efficiently and accurately detecting and identifying concealed materials are presented below.

In one or more embodiments, the system of these teachings includes a number of electromagnetic radiation sources, each electromagnetic radiation source having substantially one wavelength from a number of wavelengths, at least some of the number of wavelengths substantially coinciding with wavelengths in an absorption spectrum of predetermined materials, a patterning component disposed between the number of electromagnetic radiation sources and the area of interest, the patterning component receiving electromagnetic radiation from at least one electromagnetic radiation source from the number of electromagnetic radiation sources and providing at least a portion of the electromagnetic radiation received to an area of interest, each one of the number of the electromagnetic radiation sources sequentially illuminating the patterning component, at least one detecting component detecting incident electromagnetic radiation at a number of pixels and operatively disposed to receive an image of a region after illumination of the region by one electromagnetic radiation source from the patterning component, an analysis subsystem configured to obtain a number of pixelated images by sequentially illuminating the area of interest, illumination through the patterning component producing areas in each pixelated image that are not directly illuminated, obtain, for each one or more pixelated images from the number of pixelated images, the one or more pixelated images illuminated at substantially one wavelength, one pixelated image, labeled a global pixelated image, produced substantially by the areas are not directly illuminated, constituting a number of global pixelated images, process the number of global pixelated images; the number of global pixelated images, after processing, constituting a vector of processed data at each pixel from a number of pixels and compare, at each pixel, the vector of processed data to a predetermined vector corresponding to a predetermined material, presence of the predetermined material being determined by comparing.

In one or more embodiments, the method of these teachings includes sequentially illuminating, for a number of exposures, through a patterning component, an area of interest with electromagnetic radiation, each exposure comprising electromagnetic radiation at substantially one wavelengths from a number of wavelengths; the electromagnetic radiation being modulated with respect to time, at least some of the number of wavelengths substantially coinciding with wavelengths in an absorption spectrum of predetermined materials; at least some exposures from the number of exposures being at different wavelengths, detecting, at a number of pixels, and at each exposure, reflected/scattered electromagnetic radiation from the area of interest; the reflected/scattered electromagnetic radiation from the area of interest being detected by one or more detecting components; obtaining a number of pixelated images from the one or more detecting components, illumination through their patterning component producing areas in each pixelated image that are not directly illuminated, obtaining, for each one or more pixelated images from the number of pixelated images, the one or more pixelated images illuminated at substantially one wavelength, one pixelated image, labeled a global pixelated image, produced substantially by the areas are not directly illuminated, constituting a number of global pixelated images, processing the number of global pixelated images, the number of global pixelated images, after processing, constituting a vector of processed data at each pixel from a number of pixels and comparing, at each pixel, the vector of processed data to a predetermined vector corresponding to a predetermined material, presence of the predetermined material being determined by said comparing.

A number of other embodiments of the system and a method of these teachings are also disclosed.

For a better understanding of the present teachings, together with other and further needs thereof, reference is made to the accompanying drawings and detailed description and its scope will be pointed out in the appended claims.

BRIEF DESCRIPTION OF THE DRAWINGS

FIGS. 7a and 7b show embodiments of the method of these teachings;

FIGS. 12a, 12b show images obtained using the exemplary embodiment of FIG. 11 when there is not a patterning component (12a) and when a patterning component is used (12b)

DETAILED DESCRIPTION

Figure 1:
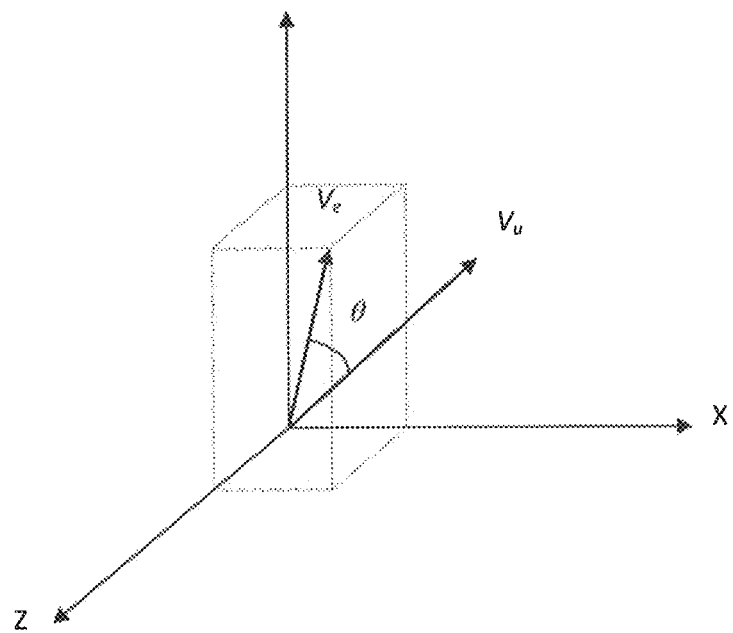
FIG. 1 shows an example vector in all vector space.

The following detailed description presents the currently contemplated modes of carrying out these teachings. The description is not to be taken in a limiting sense, but is made merely for the purpose of illustrating the general principles of these teachings.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

In order to elucidate the present teachings, the following definitions are provided.

A "projection," as used herein, is a measure of a portion of a number of values (sometimes referred as a vector) located along another number of values (sometimes referred to as another vector).

An "optical combiner," as used herein is a passive device in which emission from several sources (fibers in one embodiment) is distributed to one combination fiber.

In one or more embodiments, the system of these teachings includes a number of electromagnetic radiation sources, each electromagnetic radiation source having substantially one wavelength from a number of wavelengths, at least some of the number of wavelengths substantially coinciding with wavelengths in an absorption spectrum of predetermined materials, a patterning component disposed between the number of electromagnetic radiation sources and the area of interest, the patterning component receiving electromagnetic radiation from at least one electromagnetic radiation source from the number of electromagnetic radiation sources and providing at least a portion of the electromagnetic radiation received to an area of interest, each one of the number of the electromagnetic radiation sources sequentially illuminating the patterning component, at least one detecting component detecting incident electromagnetic radiation at a number of pixels and operatively disposed to receive an image of a region after illumination of the region by one electromagnetic radiation source emanating from the patterning component, an analysis subsystem configured to obtain a number of pixelated images by sequentially illuminating the area of interest, illumination through the patterning component producing areas in each pixelated image that are not directly illuminated, obtain, for each one or more pixelated images from the number of pixelated images, the one or more pixelated images illuminated at substantially one wavelength, one pixelated image, labeled a global pixelated image, produced substantially by the areas are not directly illuminated, constituting a number of global pixelated images, process the number of global pixelated images; the number of global pixelated images, after processing, constituting a vector of processed data at each pixel from a number of pixels and compare, at each pixel, the vector of processed data to a predetermined vector corresponding to a predetermined material, presence of the predetermined material being determined by comparing.

In one instance, each one of the number of the electromagnetic radiation sources sequentially illuminates the patterning component (also referred to as one or more masks) and the electromagnetic radiation emanating from the patterning component illuminates an area of interest. The number of electromagnetic radiation sources emit substantially from one location. The one or more pixelated image capture devices (also referred to as one or more detecting components) receive reflected/scattered electromagnetic radiation from the area of interest.

In one or more instances, the analysis subsystem (also referred to as a component) includes a background subtraction subcomponent configured for subtracting, at each pixel from the number of pixels, a background image pixel value from a pixel value for detected reflected/scattered electromagnetic radiation, the background subtraction subcomponent producing a background subtracted value at said each pixel, a ratio intensity subcomponent configured for obtaining, at each pixel, a number of ratio values, each ratio value being a ratio of a background subtracted value at one wavelength from the number of wavelengths to a background subtracted value at a selected wavelengths from the number of wavelengths, and a projection subcomponent configured for obtaining, at each pixel, a measure of a portion of the number of ratio values located along predetermined values at the number of wavelengths for said predetermined materials.

In other instances, the analysis subsystem (also referred to as a component) also includes a normalizing subcomponent configured to normalize, for each pixel, the background subtracted value at each pixel respect to a difference between a value for a measure of emission from the electromagnetic radiation source used to generate the image and a measure of background electromagnetic radiation.

Figure 3A:
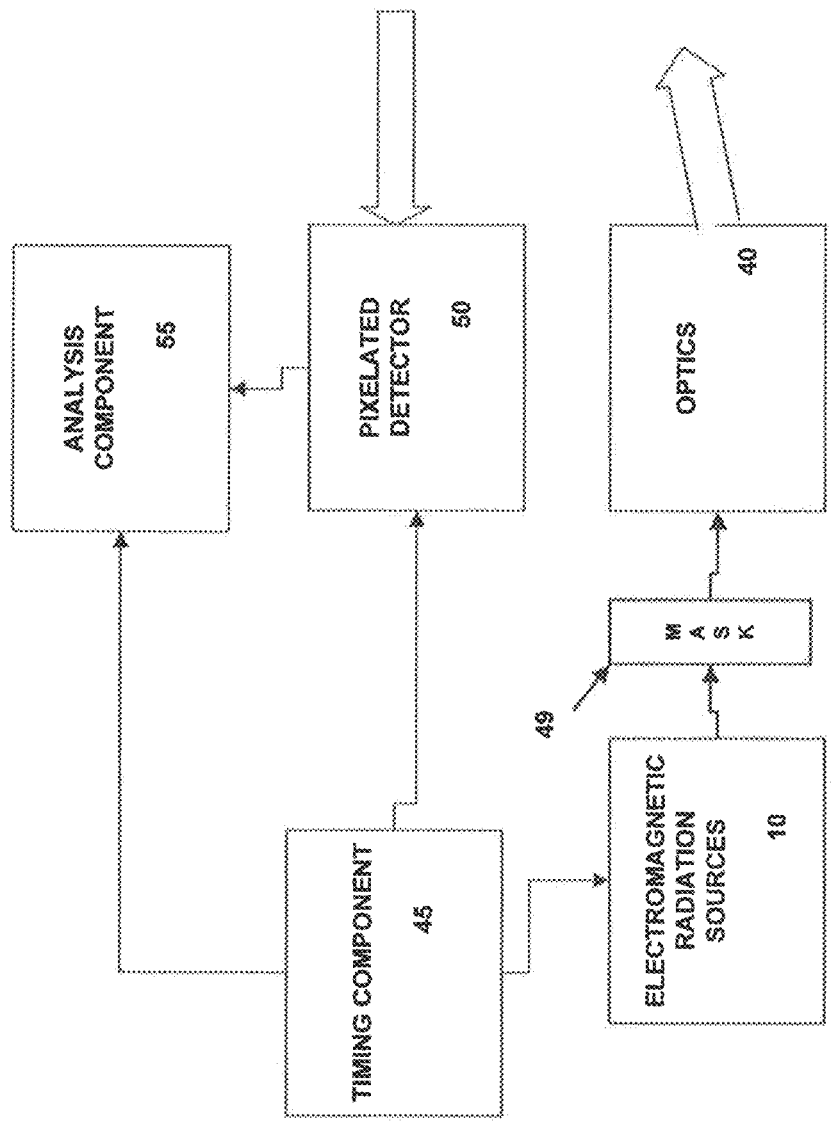
FIGS. 3a-3c show block diagram representations of the embodiments of the system of these teachings.

In one embodiment, the system of these teachings also includes a timing component providing a signal for initiation of emission from a selected one of the electromagnetic radiation sources. The timing component also provides the initiation signal for initiating detection by the pixelated image capture device A block diagram representation of an embodiment of the system of these teachings is shown in FIG. 3a. Referring to FIG. 3a, in the embodiment shown therein, each one of a number of electromagnetic radiation sources 10, each electromagnetic radiation source having substantially one wavelength from a number of wavelengths, at least some of the number of wavelengths substantially coinciding with wavelengths in an absorption spectrum of predetermined materials, sequentially illuminates the patterning component 49. The electromagnetic radiation emanating from the patterning component 49 illuminates, through an optical subsystems 40, an area of interest. The number of electromagnetic radiation sources emit substantially from one location. The scattered/reflected electromagnetic radiation from the area of interest is received by the one or more pixelated detectors 50. A timing component 45 provides the initiation signal for an electromagnetic radiation source 10 and for the pixelated detector 50 and an analysis component 55, so that the pixelated detector 50 captures the scattered/reflected electromagnetic radiation resulting from elimination by the electromagnetic radiation source 10 at substantially one wavelength and the data from pixelated detector 50 is captured by the analysis subsystem 55. After the data has been collected for all the wavelengths from the number of wavelengths and the analysis component provides at each substantially one wavelength a global pixelated image, the data, at each pixel, can be represented as a vector, data at each wavelength being data at one component of the vector. At each pixel, the vector of processed data is compared in the analysis subsystem 55, in one instance, by means of a projection, to a predetermined vector corresponding to a predetermined material, presence of the predetermined material being determined by the comparison.

Figure 2A:
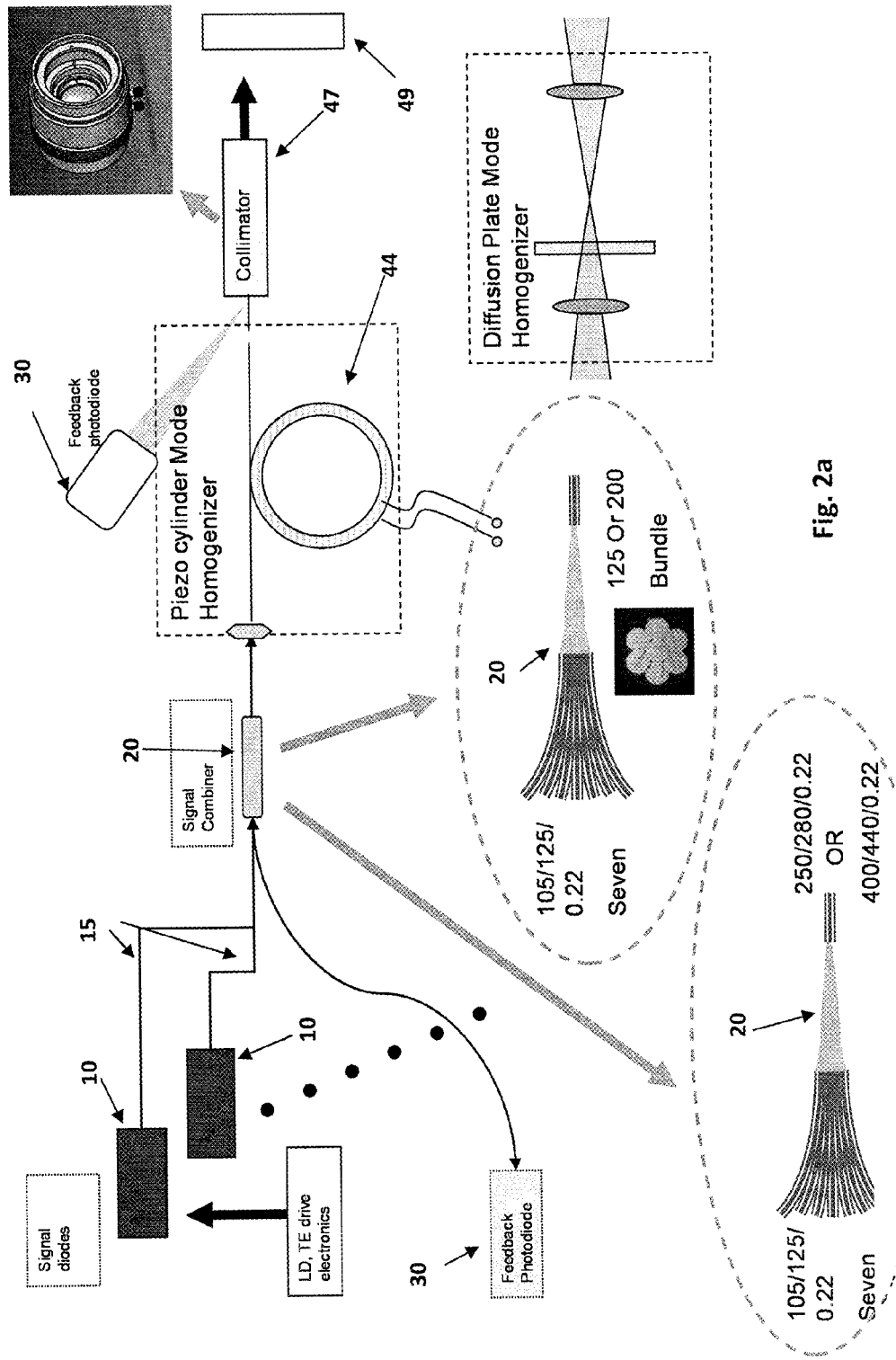
FIG. 2a shows an embodiment of the system of these teachings.
Figure 2B:
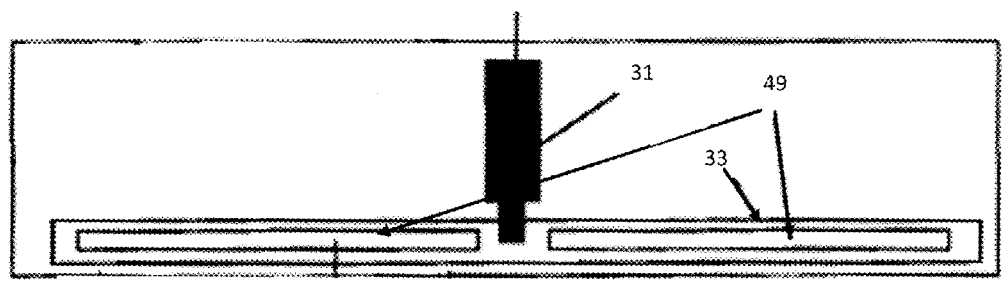
FIG. 2b shows one embodiment of a component in an embodiment of the system of these teachings.

An embodiment of the patterning component 49 is shown in FIG. 2b. As shown in FIG. 2b, the patterning component 49, in this embodiment having two or more patterns (masks), is disposed in enclosure 33 and, in one instance, the enclosure is movable. The motion inducing component 31 in one instance can be a rotation inducing component (for example, but not limited to, a rotating motor coupled to the enclosure) and, in another instance, can be a translation component (for example, but not limited to, a translating motor coupled to the enclosure). The enclosure is transparent at least in the area in front and in back of the patterning component 49.

Figure 2C:
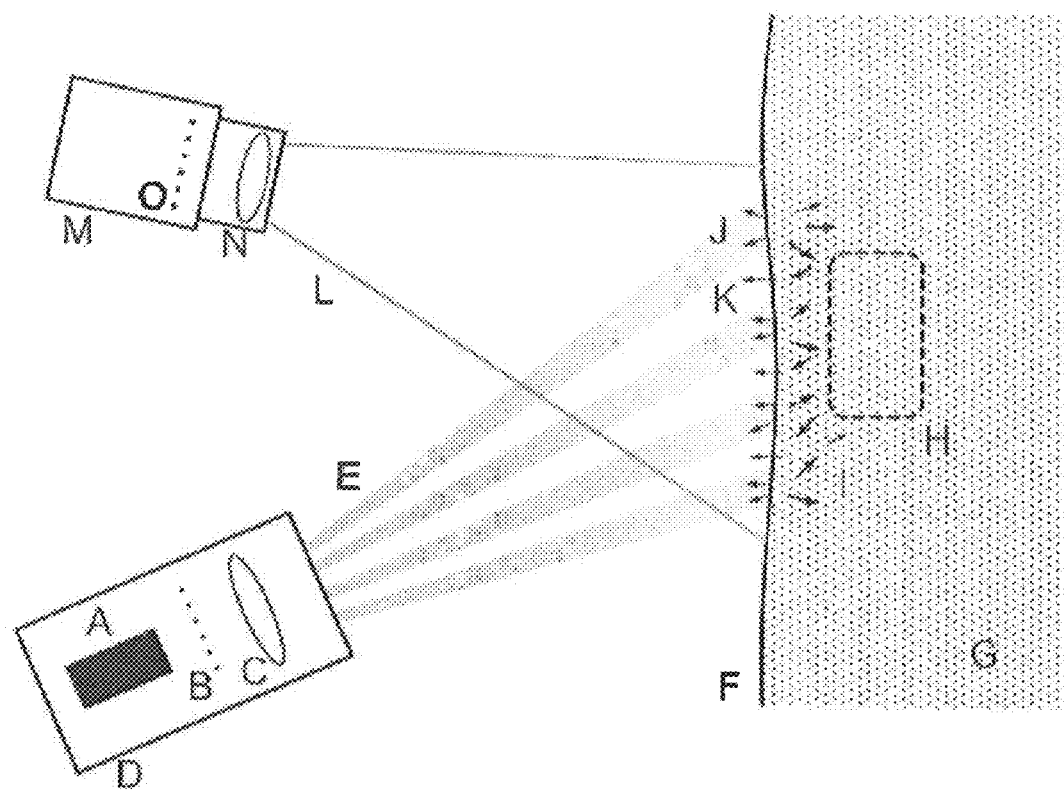
FIG. 2c shows another embodiment of the system of these teachings.

FIG. 2c shows another embodiment of the system of these teachings. In the embodiment shown in FIG. 2c, a number of electronic radiation sources A, each electromagnetic radiation source having substantially one wavelength from a number of wavelengths, at least some of the number of wavelengths substantially coinciding with wavelengths in an absorption spectrum of predetermined materials, illuminates a patterning component B and the patterned electromagnetic radiation emanating from the patterning component B is projected by one or more optical components C onto an area of interest F, including one or more concealed objects H. The electromagnetic radiation backscatter from the surface F has areas that are substantially directly illuminated K and areas that are not substantially directly illuminated J (the term substantially is used since diffraction by a patterning component would be viewed as illuminated and illuminated areas in geometric optics but it would be a continuum in physical optics). A portion of backscattered electromagnetic radiation is collected by collection optics N, which images the portion of the backscattered electromagnetic radiation onto one or more detectors O. The detection system M in one embodiment is one or more detection systems.

Figure 3B:
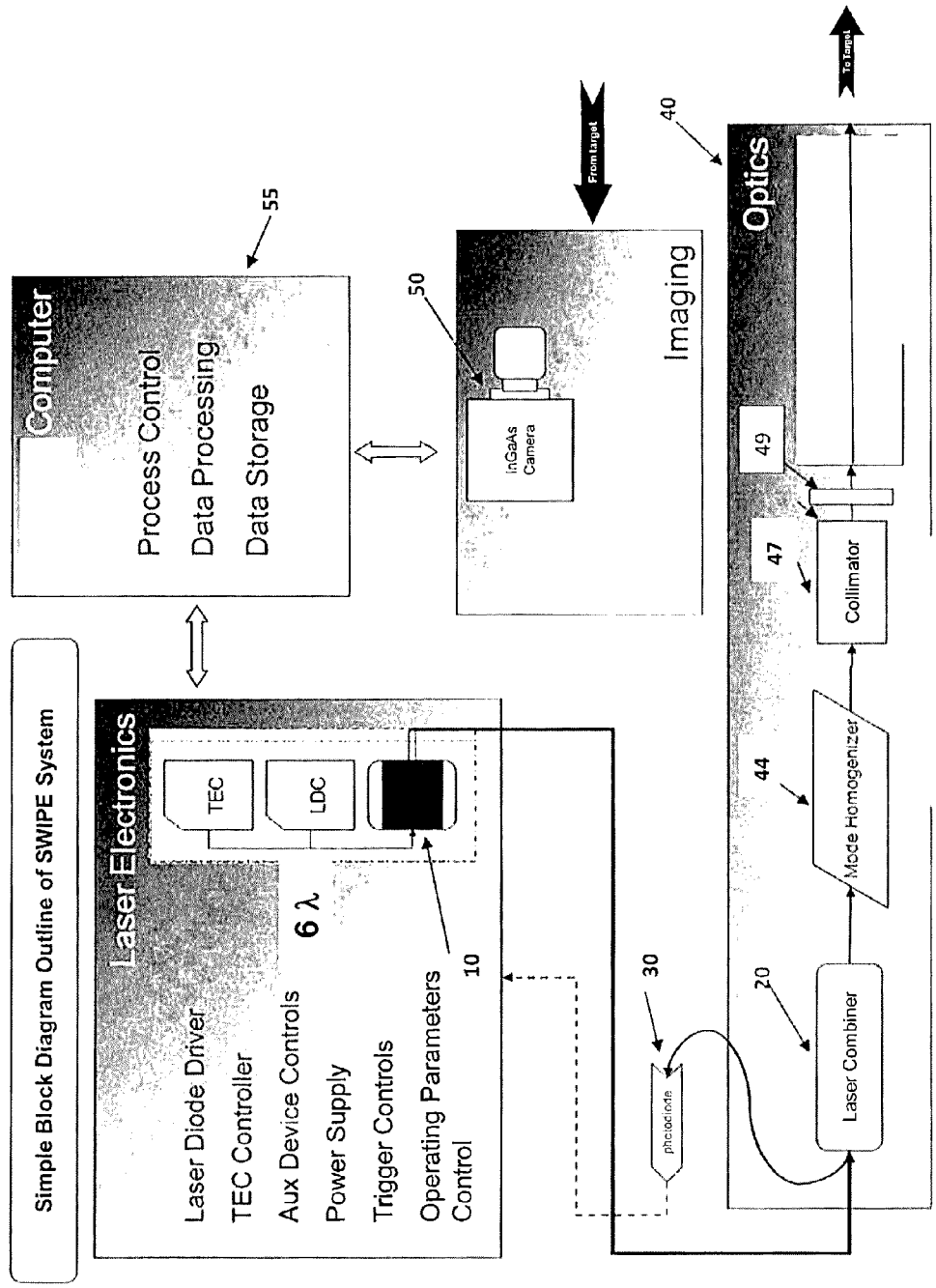
Figure 3C:
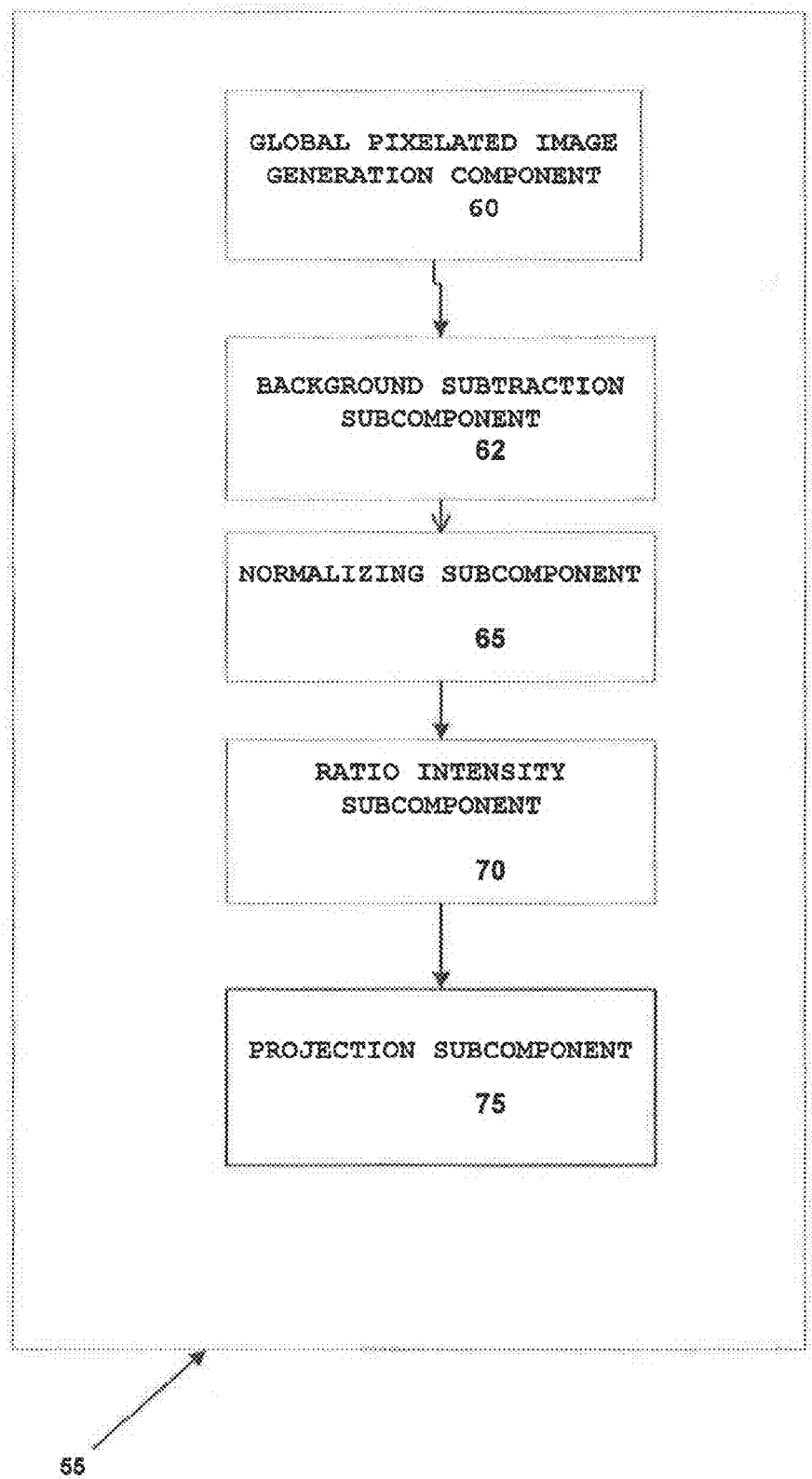

FIG. 3c shows an embodiment of a portion of the analysis subsystem 55. Referring to FIG. 3c, in the embodiment shown therein, the analysis subsystem 55 includes a global pixelated image generation subcomponent 60, a background subtraction subcomponent 62, a normalizing subcomponent 65, a ratio intensity subcomponent 70 and a projection subcomponent 75. The global pixelated image generation component 60 is configured to obtain, for each one or more pixelated images from the number of pixelated images, the one or more pixelated images illuminated at substantially one wavelength, one pixelated image, labeled a global pixelated image, produced substantially by the areas are not directly illuminated, and thereby constituting a number of global pixelated images The background subtraction subcomponent 60 is configured for subtracting, at each pixel from the number of pixels, a background image pixel value from a pixel value for detected reflected/scattered electromagnetic radiation, the background subtraction subcomponent producing a background subtracted value at said each pixel. The normalizing subcomponent 65 is configured to normalize, for each pixel, the background subtracted value at each pixel with respect to a difference between a value for a measure of emission from the electromagnetic radiation source used to generate the image and a measure of background electromagnetic radiation. In one instance, the measure of emission from the electromagnetic radiation source is selected so that normalization compensates for the $1/r^2$ dependence of the scattered radiation. (In one embodiment, this is accomplished by using the wavelengths at which a concealed object of interest does not substantially absorb the emission from the electromagnetic radiation source.) The ratio intensity subcomponent 70 is configured for obtaining, at each pixel, a number of ratio values, each ratio value being a ratio of a background subtracted normalized value at one wavelength from the number of wavelengths to a background subtracted normalized value at a selected wavelength from the number of wavelengths. The projection subcomponent 75 is configured for obtaining, at each pixel, a measure of a portion of the number of ratio values located along predetermined values at the number of wavelengths for said predetermined materials (which is equivalent to the definition of a projection).

In one instance, the global pixelated image generation component 60 is configured to obtain at least two detected images and obtain said one global pixelated image from the at least two detected images. In one embodiment of that instance, two detected images are used and the two images include two complementary images.

In one embodiment of the above instance, (as detailed by S. K. Nayar et al., "Fast Separation of Direct and Global Components of a Scene using High Frequency Illumination," ACM Transactions on Graphics (TOG)—Proceedings of ACM SIGGRAPH 2006, #25, Issue #3, July 2006, pg. 935-944, which is incorporated, by reference herein in its entirety and for all purposes) the first image L+ is an image of the area of interest where a fraction α of the pixels are directly illuminated, and the second image L− is an image where the area of interest is illuminated, with complementary illumination, that the fraction of pixels are directly illuminated keys 1−α. If the pixel i is lit directly by the source in the first image then it is not lit by the source in the second image, and the intensity of each of the is described by $$L^+[c,i]=L_d[c,i]=\alpha L_g[c,i], L^-[c,i]=(1-\alpha)L_g[c,i], \quad (1)$$

Where $L_d[c,i]$ is the contribution to the image by the directly illuminated pixels and $L_g[c,i]$ is the contribution to the image by the pixels are not directly illuminated (also referred to as the pixelated global image), If the fraction α is known, the direct and global components at each pixel from can be computed from two images. In the above, it has been assumed that when a source pixel is not activated it does not generate any light. In the many instances, for example, this is seldom completely true. If the brightness of a deactivated source element is denoted by a fraction b, where 0<b<1, of an activated element, then the above expressions can be modified as $$L^+=[c,i]=L_d[c,i]+\alpha L_g[c,i]+b(1-\alpha)L_g[c,i],$$
$$L^-[c,i]=bL_d[c,i]+(1-\alpha)L_g[c,i]+\alpha b L_g[c,i]. \quad (2)$$

Again, if α and b are known, the separation can be done using just two images. The fraction α can be approximated by the fraction of the mask that is covered by the opaque or blocking sections. The fraction b can be approximated by the results of calculations.

In another instance, the global pixelated image generation component 60 is configured to obtain one detected image and obtain the one global pixelated image from the one detected image. The one detected image is detected at a resolution higher than that needed for the direct and global images. The direct and global images can be computed at a lower resolution using a one detected image. The one detected image is filtered to find local peaks and valleys. In one instance, a pixel is assigned a maximum or minimum label if its brightness is the maximum or minimum within an n x in window around it. The brightness at these peaks and valleys are interpolated to obtain full resolution $L_{max}$ and $L_{min}$ images. The separation results are computed at 1/k of the resolution of the captured image. Then, $L_{max}$ and $L_{min}$ images are computed at this lower resolution by averaging their values within k×k blocks in the high resolution images. Once this is done, $L_d$ and $L_g$ are computed using Equation 1.

It should be noted that other embodiments in which two detected images are used are also within the scope of these teachings. In one instance, one of the images is processed to identify the valleys (minima) and regions in a neighborhood of the valleys are set zero. That one image is subtracted from the other image to obtain the global pixelated image, $L_g[c,i]$.

It should be noted that other embodiments in which the analysis subsystem 55 includes a global pixelated image generation subcomponent 60 and a ratio intensity subcomponent 70 are within the scope of these teachings. The ratio intensity subcomponent 70 is configured for obtaining, at each pixel, a number of ratio values, each ratio value being a ratio of a value at one wavelength from the number of wavelengths to a value at a selected wavelength from the number of wavelengths.

In one instance, the system of these teachings also includes an electromagnetic emission monitoring component. The timing component provides the initiation signal for initiating monitoring, using the monitoring component, of electromagnetic emission from the selected one of the electromagnetic radiation sources.

In one embodiment, emission substantially from one location for the electromagnetic radiation sources is enabled by means of an optical subsystem. In one instance, the optical subsystem has fiber optic pigtails optically coupled to each electromagnetic radiation source and an optical combiner receiving radiation from the fiber optic pigtails. In another instance, the optical subsystem includes a number of dichroic beam splitters, each dichroic beam splitter receiving electromagnetic radiation from one or more of electromagnetic radiation sources and an optical fiber receiving electromagnetic radiation from the number of dichroic beam splitters.

In one embodiment, the analysis component includes one or more processors and one or more computer usable media having computer readable code embodied therein, the computer readable code causing the one or more processors to subtract, at each pixel, a background image pixel value from a pixel value for detected reflected/scattered electromagnetic radiation, subtraction producing a background subtracted value at said each pixel, obtain, at each pixel, a number of ratio values, each ratio value being a ratio of a background subtracted value at one wavelength to a background subtracted value at a selected wavelength from the number of wavelengths and obtain, at each pixel, a measure of a portion of the number of ratio values located along predetermined values at the number of wavelengths for the predetermined materials.

In one instance, the computer readable code also causes the one or more processors to normalize, for each pixel, the background subtracted value at each pixel with respect to a difference between a value for a measure of emission from one of the electromagnetic radiation sources and a measure of background electromagnetic radiation.

In one embodiment, one or more processors 120 are operatively connected to a component 110 allowing receiving input from the pixelated detector 50 and to computer usable media 130 having computer readable code embodied therein, where the computer readable code causes the one or more processors to implement the method of these teachings for detecting concealed objects. In one instance, the one or more processors 120 are operatively connected by means of a computer connection component (such as a computer bus) 135.

In one embodiment, the subcomponents of FIG. 3c are configured for performing their specific function by the computer readable code, embodied in the computer usable media 130, causing the one or more processors 120 to perform the specific function.

Figure 8:
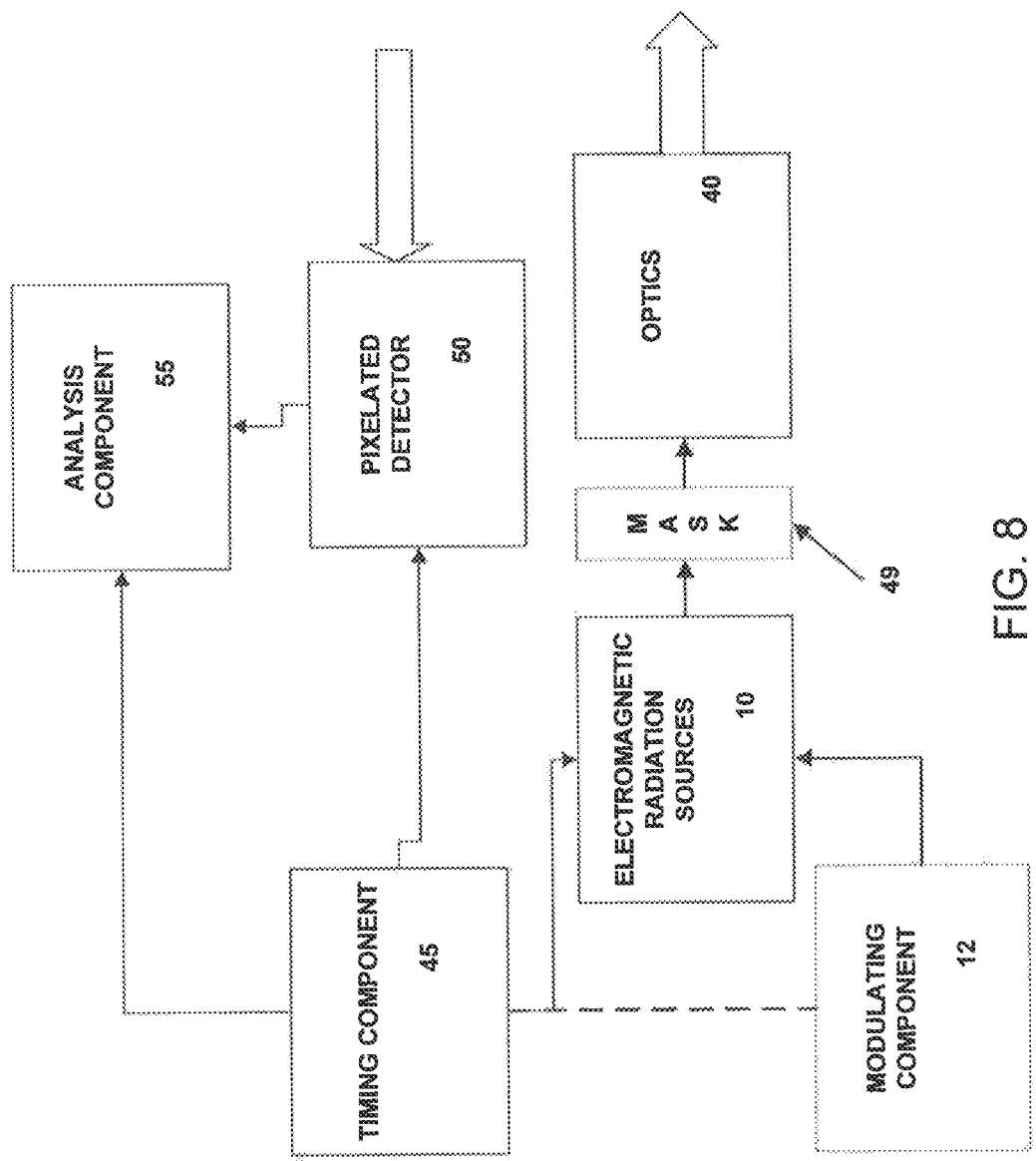
FIG. 8 shows a block diagram representation of another embodiment of the system of these teachings.

In another embodiment, the system of these teachings includes a modulating component that modulates, with respect to time, the emission of each electromagnetic radiation source. The modulated emission has time varying and DC component. FIG. 8 shows a block diagram representation of the embodiments including a modulating component. As shown in FIG. 8, the modulating component 12 is operatively connected to the electromagnetic radiation source in order to produce a modulated electromagnetic radiation emission. The block diagram representation shown in FIG. 8 is not meant to limit the configuration of the modulating component 12 with respect to the electromagnetic radiation sources 10.

Figure 9A:
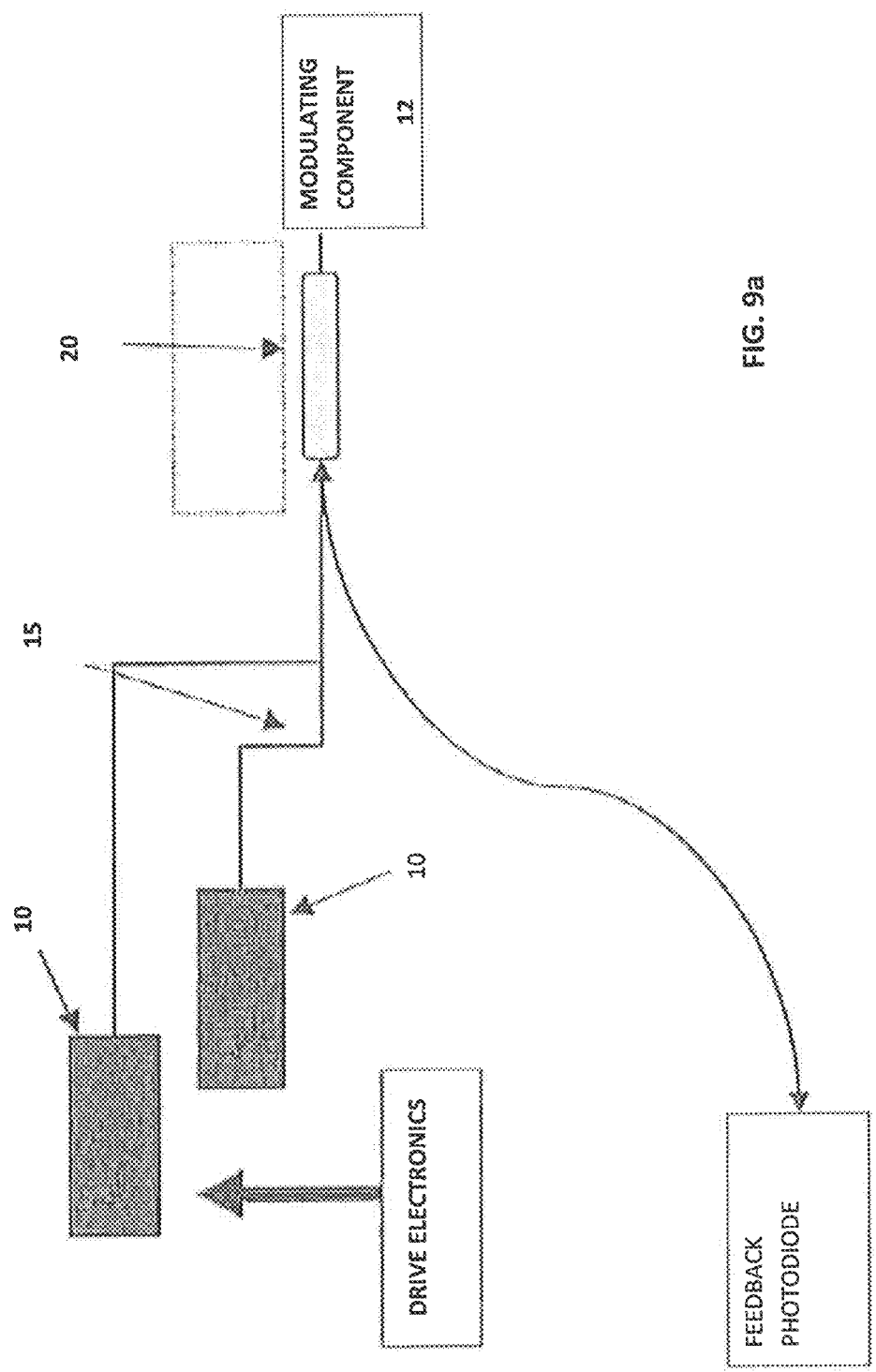
FIGS. 9a-9c show a portion of further embodiments of the system of these teachings.
Figure 9B:
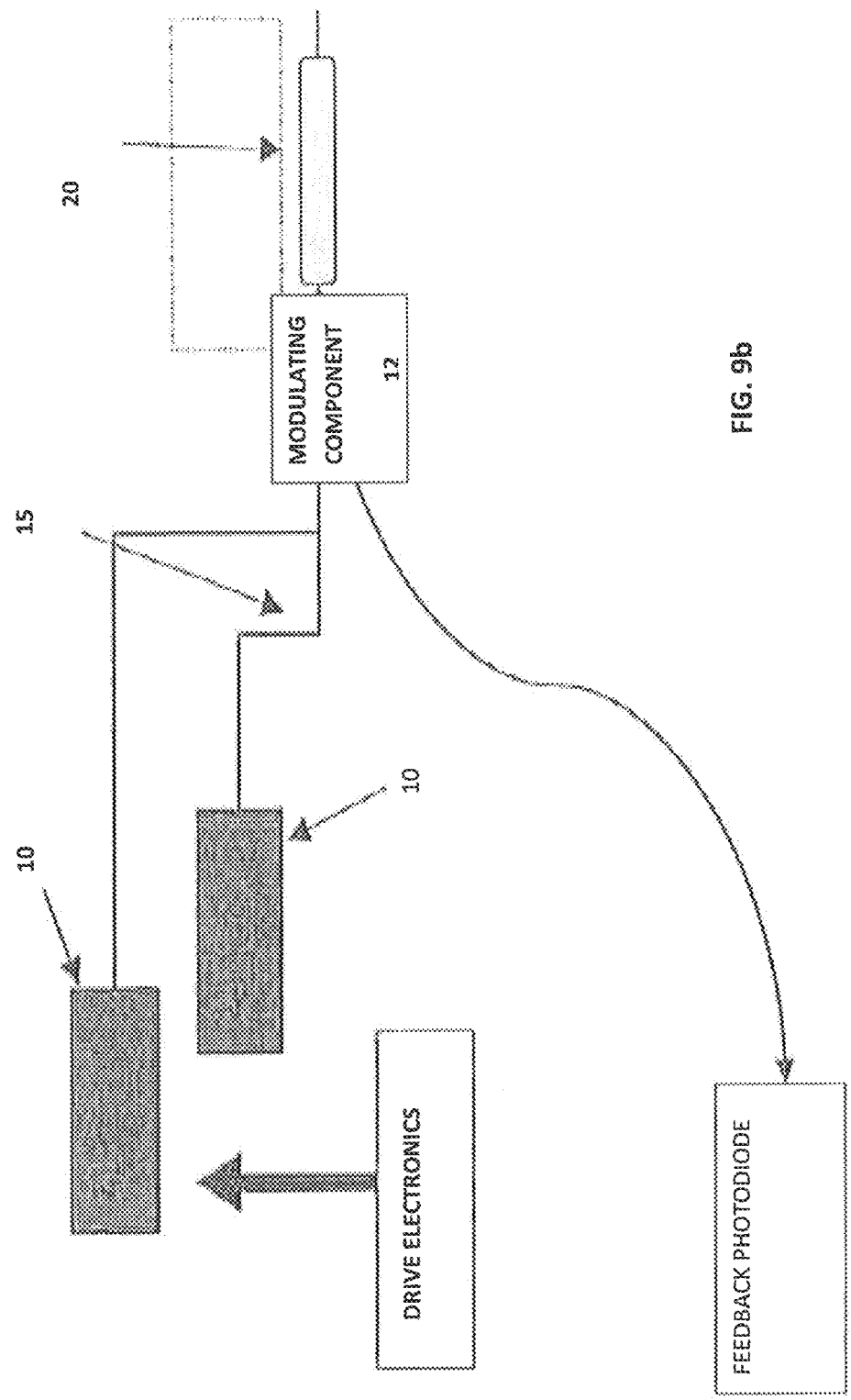
Figure 9C:
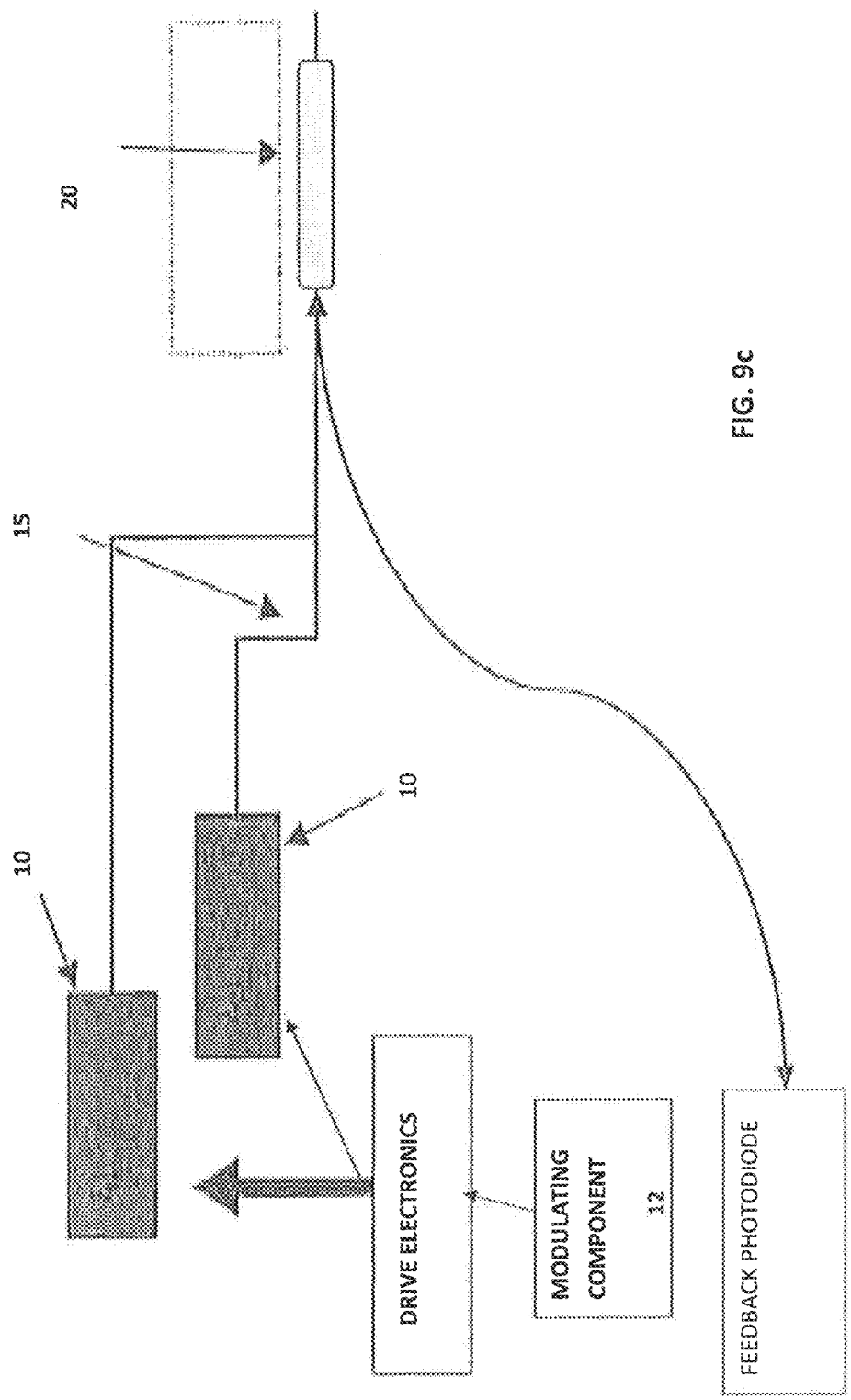

FIGS. 9a-9c show different configurations of the electromagnetic radiation sources 10 and the modulating component 12. It should be noted that these teachings are not limited to only the embodiments shown in FIGS. 9a-9c, In the embodiment shown in FIG. 9a, the modulating component is located after the beam combiner 20. In the embodiment shown in FIG. 9b, the modulating component 12 is located before the beam combiner 20. Some exemplary embodiments, these teachings not being limited only to the exemplary embodiments, of the modulating component 12 such as that used in FIGS. 9a and 9b are mechanical devices, such as a chopper wheel (a chopper wheel, in one instance is similar to the filter wheel in U.S. Pat. No. 7,328,060, Incorporated by reference herein is entirety and for all purposes, where some of the filters are clear and other filters are completely opaque), electro-optic modulators (for example, the modulators described in U.S. Pat. Nos. 6,330, 097, 3,719,414, 3,429,636, in Yariv, Optical Electronics, 3rd edition, pp, 274-306, ISBN 0-03-070289-5, 1985 and in Hetch, Optics, pp, 314-321, ISBN 0-201-11609-X, 1974, all of which are Incorporated by reference herein in their entirety and for all purposes), and acousto-optic modulators (for example, those described in U.S. Pat. Nos. 4,759,613, 7,385,749, and in Yariv, Optical Electronics, 3rd edition, pp, 385-401, ISBN 0-03-070289-5, 1985, all of which are incorporated by reference herein in their entirety and for all purposes). The choice of modulator depends on availability, the type of electromagnetic radiation source used and the ease of providing multiple wavelengths. Embodiments in which the modulating component 12 is included in the laser cavity, for example in a Q switched laser, are also within the scope of these teachings, FIG. 9c shows an embodiment in which the modulating component 12 is connected to or is a part of the drive electronics. Diode lasers can be modulated by modulating the drive current. (See, for example, these teachings not being limited only to these examples, U.S. Pat. Nos. 7,570, 680, 5,651,017, 6,072,816, all of which are Incorporated by reference herein in their entirety and for all purposes).

In some instances, direct or indirect sunlight or incandescent light can introduce noise indeed detection process by producing signals of large magnitude. In embodiments in which the detecting component includes a photo detection subcomponent and an electronic readout subcomponent. The high ambient light contribution from direct or indirect sunlight or incandescent light can be countered by use of short image integration times in order to avoid saturation in the electronic readout subcomponent. However, the short integration times can present a limit to the amount of scattered light acquired during image capture. In one embodiment, the detecting component includes a photo detection subcomponent receiving the reflected/scattered electromagnetic radiation from the area of interest and providing an electrical signal and an electronic readout subcomponent receiving the electrical signal. The photo detection subcomponent is AC coupled to the electronic readout subcomponent. AC coupling can eliminate or greatly reduce the DC ambient light contribution from direct or indirect sunlight or incandescent light.

Figure 10:
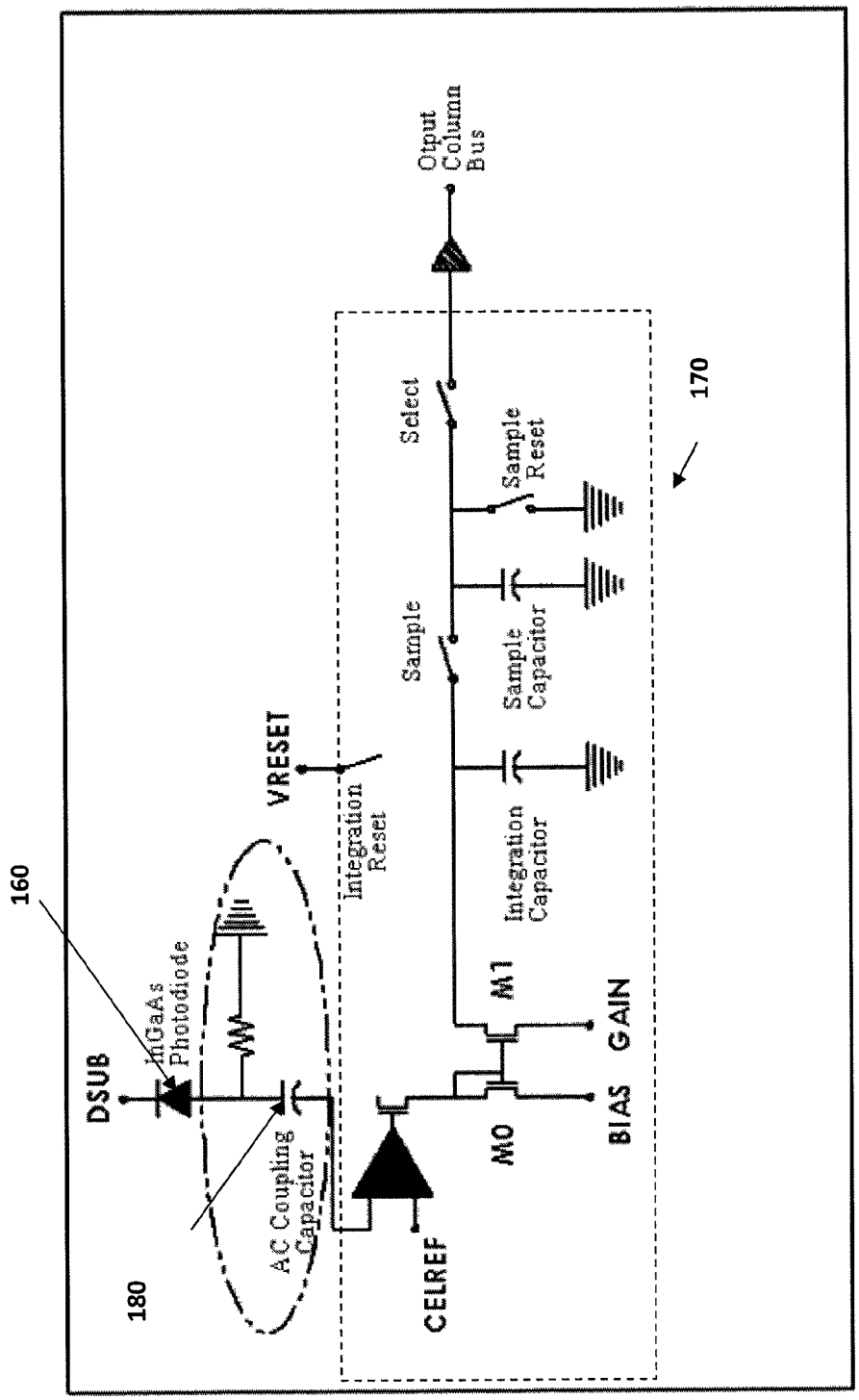
FIG. 10 shows the detecting component in one embodiment of the system of these teachings.

FIG. 10 shows an exemplary embodiment of a detecting component including a photo detection subcomponent 160 (a photo diode in the embodiment shown) providing an electrical signal after receiving electromagnetic radiation and an electronic readout subcomponent 170 receiving the electrical signal, where the photo detection subcomponent 160 is AC coupled, by means of a capacitor 180, to the electronic readout subcomponent 170.

In yet another embodiment, the system of these teachings includes a housing. In one instance, the housing has a top portion and a handle portion. The top portion has an opening at one end and a section extending away from that end. The pixelated detection component (image acquisition device) is disposed inside the house and optically disposed to receive reflected/scattered electromagnetic radiation from the area of interest through the opening. The electromagnetic radiation sources are optically disposed such that the electromagnetic radiation sources illuminate the area of interest through the opening. Weight and dimensions of the housing and components in the housing are selected to enable the housing to be handheld. The housing is operatively connected to the analysis component and to timing and power components. In one instance, the weight of the housing and components in the housing is less than 10 pounds, preferably less than 4 pounds.

Figure 6A:
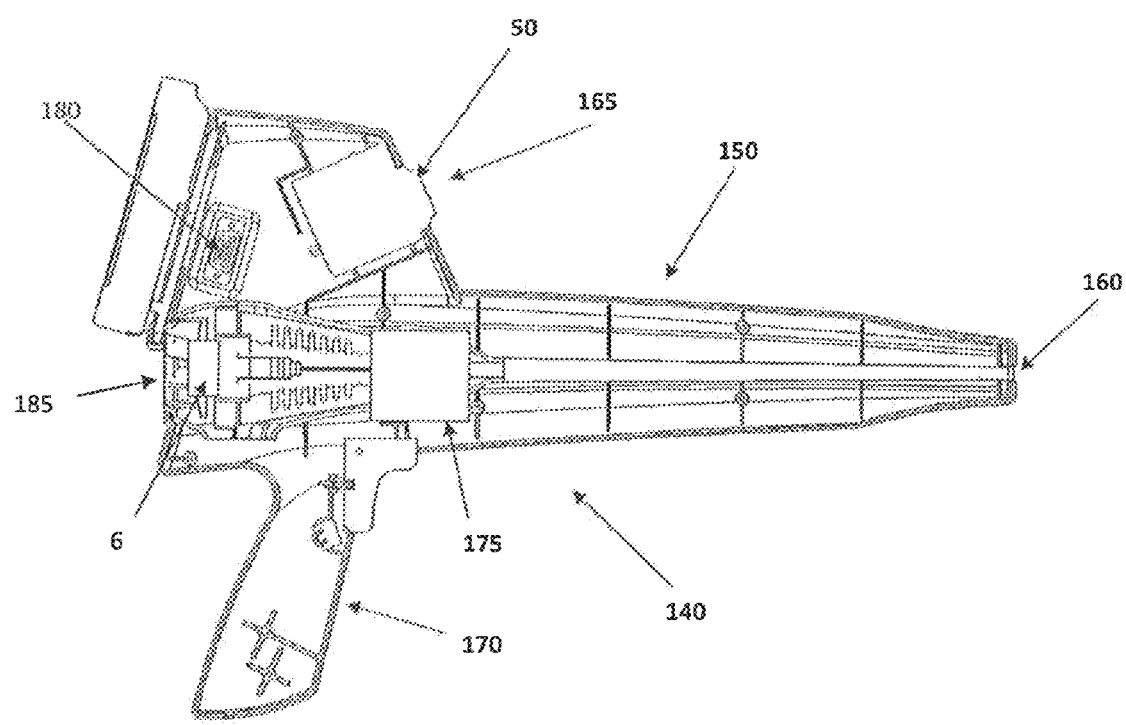
FIGS. 6a-6b show a portion of a portable embodiment of the system of these teachings.

FIG. 6a shows a portion of one embodiment of a portable system of these teachings including a housing. Referring to FIG. 6a, in the embodiment shown therein, the housing 140 has a top portion 150 and a handle portion 170. The top portion has an opening 160 at one end and a section extending away from that end. The pixelated detector 50 is disposed in that housing and optically disposed to receive, either through opening 160 and optic components 175 or through another opening 165, the scattered/reflected electromagnetic radiation from the area of interest. The electromagnetic radiation sources are optically disposed, either by being this post in the housing 140, as a component 6, or by being optically connected by an optical connection 185 to the housing 140, such that the electromagnetic radiation sources illuminate the area of interest through the opening. The data and timing signals can be exchanged through an electrical connector 180. A similar connector provides power signals.

Figure 6B:
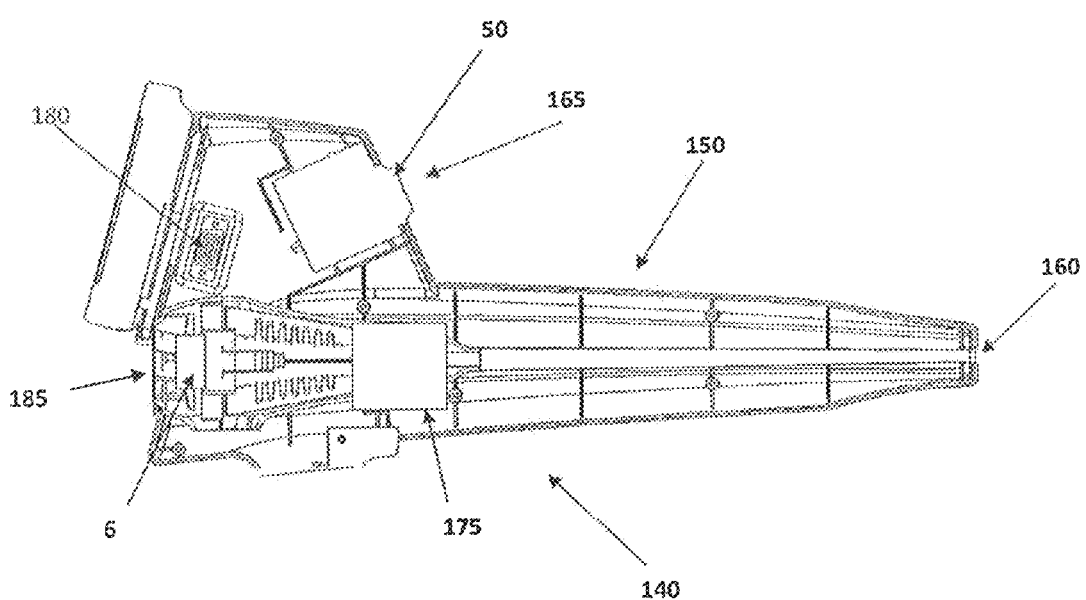

FIG. 6b shows another embodiment of the housing 140. In the embodiment shown in FIG. 6b, the handle portion is embodied in the top portion 150.

The electromagnetic radiation sources 10 used in the embodiments of the system of these teachings can be any of a wide range of electromagnetic radiation sources, such as, but not limited to, light emitting diodes, lasers, laser diodes and other electromagnetic radiation sources.

The choice of wavelengths in embodiments of the system of these teachings is determined by an expeditious and efficient system design based on considerations such as what components are best suited for the application, availability of components and, in some cases, cost of components. There is no inherent limitation as to the choice of wavelengths in the embodiments of the system of these teachings.

In order to better illustrate the present teachings, exemplary embodiments are disclosed hereinbelow. It should be noted that these teachings are not limited to this exemplary embodiment and that numerical values presented are presented for illustration purposes and not in order to limit the present teachings.

It should be noted that these teachings are not limited to the choice of electromagnetic radiation sources, wavelengths and detecting component used in the exemplary embodiment.

Although one of the exemplary embodiments shown hereinbelow relates to detecting explosives, it should be noted that other materials are also within the scope of these teachings.

One exemplary embodiment of the system of these teachings includes an infrared camera (an example of a detecting component or image acquisition component), a shortwave infrared (SWIR) camera in the exemplary embodiment, a set of laser sources (an example of electromagnetic radiation sources), laser diodes in the exemplary embodiment, that are used to illuminate the area under surveillance, and a reference photodetector that monitors the level of laser light launched by the source. In the exemplary embodiment, each laser diode has substantially a different emission wavelength within the spectral range about 0.9 to about 2 micron. The number of laser diodes can vary from 2 to 10 depending on the level of spectral identification required. The lasers are fired sequentially so that the illuminated area is bathed in light of only substantially one wavelength at a time. The individual laser diode signals are made to emit from substantially a common location to control the uniformity of illumination in the area under surveillance. This can be accomplished, in one instance, these teachings not be limited to only that instance, using fiber optic pigtailed laser diodes and a fiber optic combiner or, in another instance, constructing a laser module in which the laser diode beams all fed into a single fiber optic using a series of dichroic beamsplitters. One embodiment of the components of the system of these teachings that ensure that individual laser diodes emit from substantially one location is shown in FIG. 2a. Referring to FIG. 2a, in the exemplary embodiment shown therein, laser diodes (electromagnetic radiation sources) 10 are optically connected to optical components 15, fiber-optic pigtails in one embodiment, that provide the emitted electromagnetic radiation to a combiner component 20. A mode homogenizer 44 and a collimator 47 are subcomponents in the optical subsystem 40. A feedback photodiode (radiation monitoring component) 30 can detect the electromagnetic radiation provided by the collimator 47 or, in another embodiment, can detect the electromagnetic, radiation provided to the combiner 20.

A block diagram representation of the one exemplary embodiment of the system of these teachings is shown in FIG. 3b. Referring to FIG. 3b, in the exemplary embodiment shown therein, laser diodes 10 provide electromagnetic radiation through fiber pigtails 15 to a laser combiner 20. Electromagnetic radiation provided to the laser combiner 20 is monitored by the photodiode 30. The electromagnetic radiation provided by one laser diode 10 is delivered through the optical component 40 to area of interest. The optical component 40 includes a mode homogenizer 44 and a collimator 47. The electromagnetic radiation scattered/reflected from the area of interest is collected by the pixelated detection component 50 (a shortwave infrared (SWIR) camera in the exemplary embodiment). The pixelated data is provided to the analysis component 55.

Figure 4:
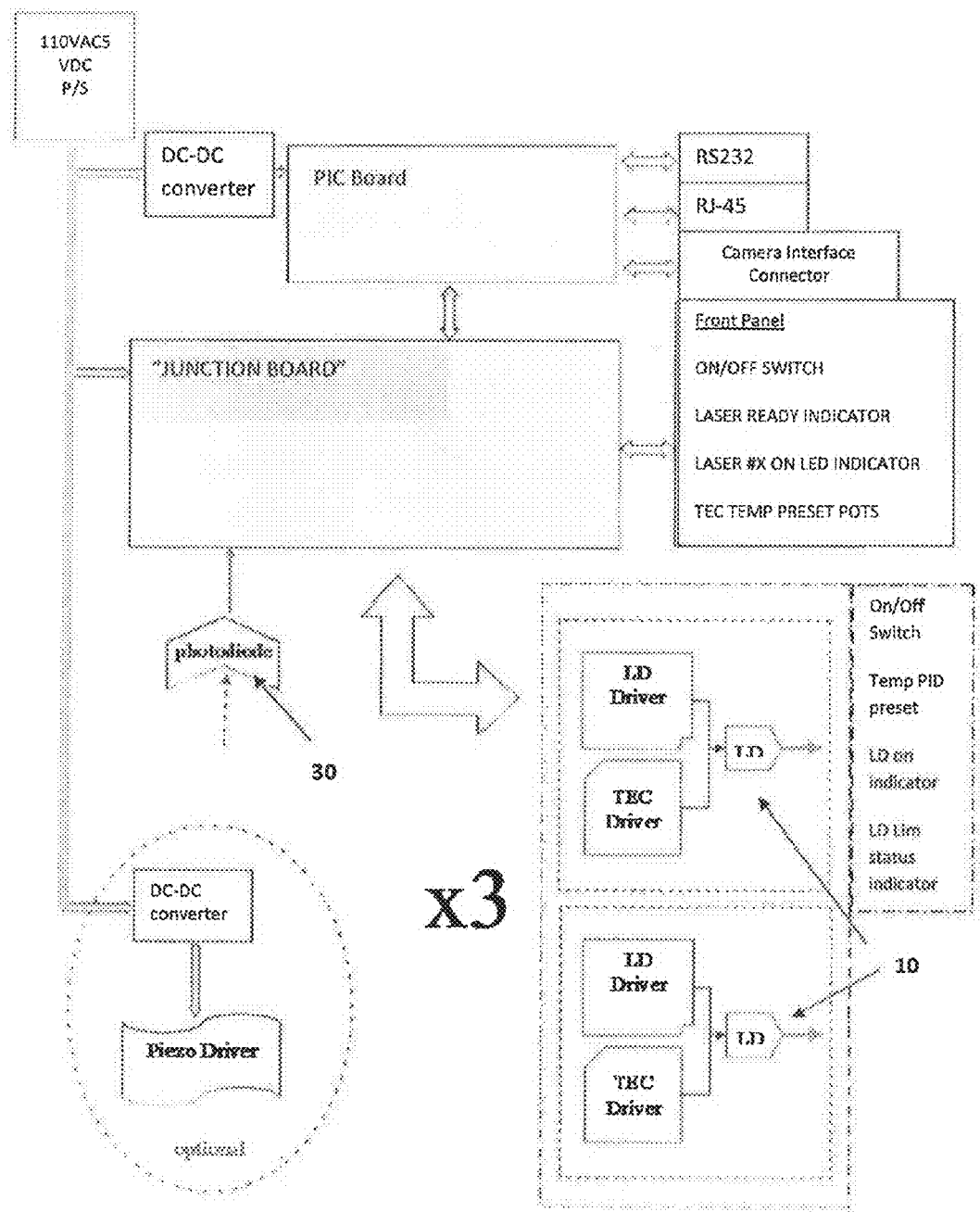
FIG. 4 shows a high-level block diagram of the electronics in the exemplary embodiment.
Figure 5:
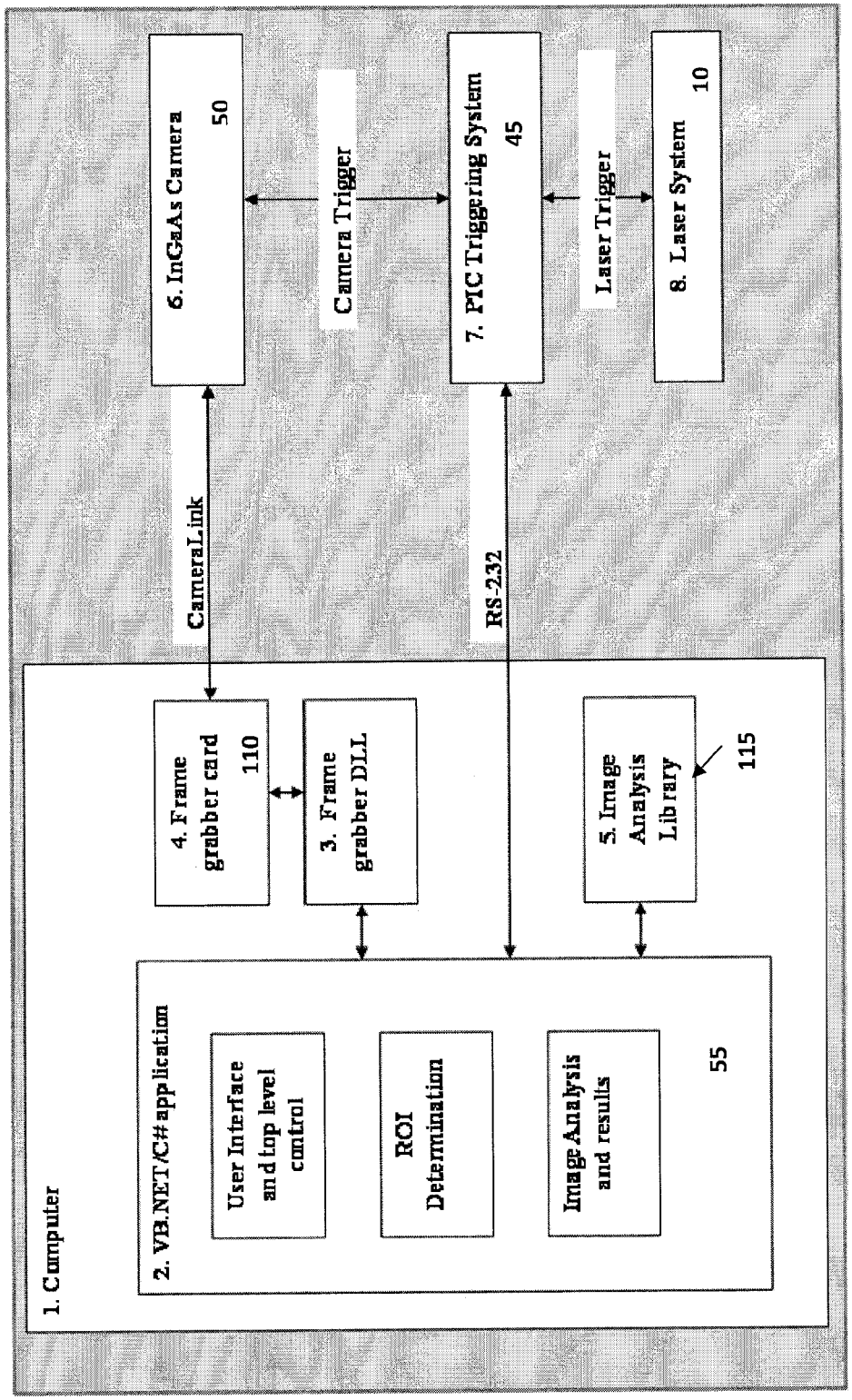
FIG. 5 shows an electrical and software block diagram of the exemplary embodiment.

An electronic trigger signal is used to trigger the laser diodes. A high-level block diagram of the electronics in the exemplary embodiment is shown in FIG. 4. The same trigger signal is also used to trigger the capture of an image with the SWIR camera and the capture of a reference photodetector 30 reading of the laser's launched power. The image is composed of a digital array of numbers representing the intensity of the light scatter from objects within the area of surveillance for the laser that was fired during its collection. Each member of the array is, in one instance, not a limitation of these teachings, a 14 bit reading acquired from a pixel of the camera's detector. A background image may also be collected to correct for any ambient light contribution to the acquired image. The reference photodetector signal is also digitized and stored along with the data array for that particular laser's image.

The number of members in the array depends on the type of camera being used. The camera in the exemplary embodiment has an array of 320 by 256 pixels; however cameras with larger or smaller arrays could also be used. The image data collected at each of the different wavelengths is treated as an array of numbers throughout the data processing steps used to generate the final result. The data processing steps are performed on a pixel-by-pixel basis across the collected images. This means that an operation like background subtraction is performed by subtracting a given pixel's value from the background image from the corresponding pixel of an image collected with the laser firing. Any operation generates a new array which contains the same number of elements as the array on which it was performed. The new array can be used to produce a new image by converting the value of each element of the array to a grey scale tint.

The laser wavelengths are selected so that a few of them coincide with regions of the spectrum where the material of interest, in one instance, explosives of interest, absorb electromagnetic radiation and others where the explosives have minimal absorption. Image data collected with the lasers having wavelengths where little to no absorption is observed are used to correct for the distance dependence of reflected light intensity (i.e., for non collimated light intensity drops off in proportion to $1/r^2$ where r is the distance from the light source).

Figure 11:
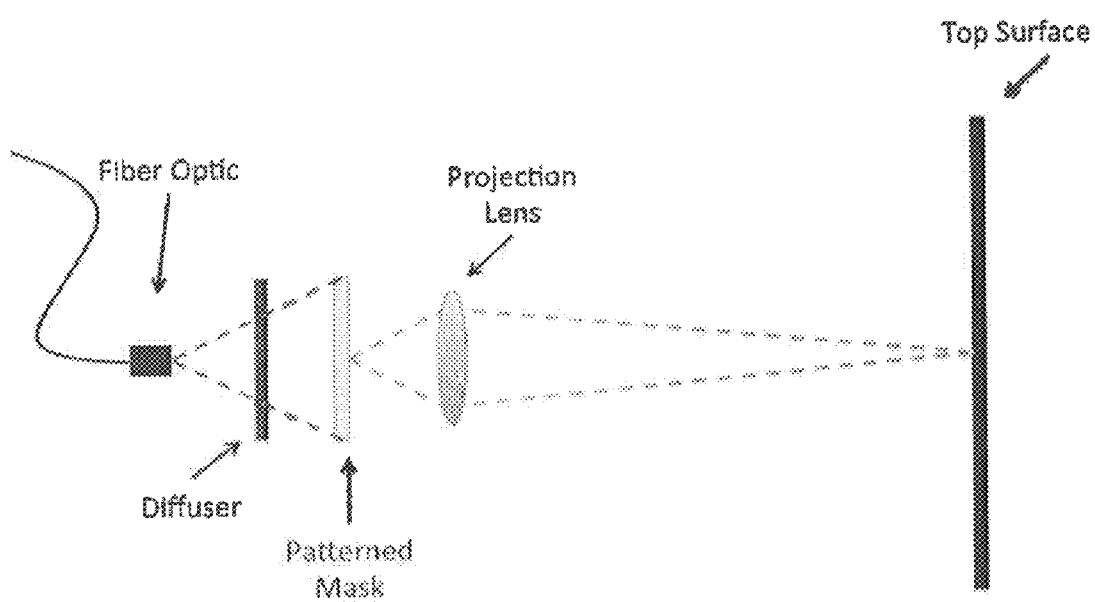
FIG. 11 shows another exemplary embodiment of the system of these teachings.

Another exemplary embodiment illustrating the detection of a package concealed below cloth layers from a stand-off distance is disclosed hereinbelow. A system has been constructed for detecting specific packages from a standoff distance concealed below cloth layers. Multiple lasers illuminate the area of interest on a top surface with different wavelengths in sequence. The top surface consists of one or more layers of wool cloth. A test package is placed below the wool layers. A diffuser serves to spread the laser light. A patterned mask consists of a wire mesh that blocks and transmits light in a regular pattern. A project lens projects an image of the mesh on the top surface creating a pattern of light and dark areas (See FIG. 11). The reflected light is imaged by a camera at 3 meters standoff distance with an imaging lens.

FIG. 12a shows an image of the reflected light at the first wavelength without the patterning. FIG. 12b shows an image of the reflected light at the first wavelength with the patterned illumination. Note that the intensity in the brightly illuminated areas was increased in the patterned case to also increase the amount of subsurface contribution from the dimly illuminated areas. The package in this case specifically absorbs at the first wavelength illuminated and does not absorb at the second wavelength. However, the absorption is small and can be clouded by other attenuation factors such as different amounts of scattering by the surface. Since the other attenuation factors are expected to be similar for both wavelengths, multispectral sensing calls for the use of multiple wavelengths to resolve the attenuation due to a specific absorption feature of the package. Collecting data with the first and second wavelength, a ratio image can be formed by dividing each pixel value from illumination with the first wavelength with each pixel value resulting from illumination with the second wavelength. The resulting ratio image shows the relative absorption between the first and second wavelengths.

Figure 13A:
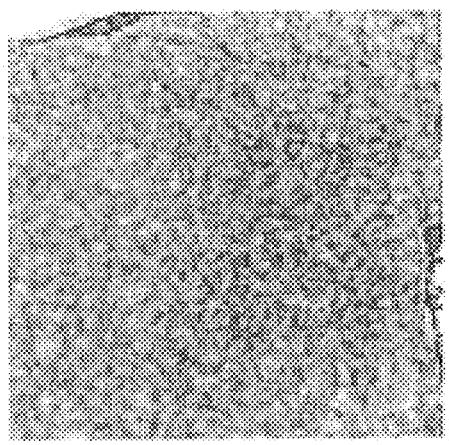
FIGS. 13a, 13b show processed images obtained from the images obtained using the exemplary embodiment of FIG. 11 when there is not a patterning component (13a) and when a patterning component is used (13b).
Figure 13B:
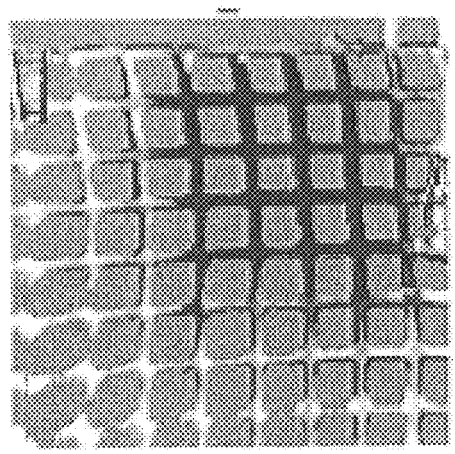

FIG. 13a shows the ratio images for standard (non-patterned) illumination. The small amount of absorption is hard to observe in this image. Additional measurements showed that the top surface reflection in this case is about 90% (this measurement can be used to estimate "b" in equation 1). The top surface reflection does not penetrate the cloth and therefore makes observing the small amount of absorption in the light that does penetrate more difficult. FIG. 13b shows the ratio images for the patterned illumination. In this case, considering the areas that were dimly illuminated in FIG. 12b, the specific absorption due to the presence of the package is observable as dark pixels in the upper right quadrant of the image.

An embodiment of the method of these teachings is shown in FIG. 7a. In the embodiment shown in FIG. 7a, the method of these teachings includes sequentially illuminating, through a patterning component, for a number of exposures, an area of interest with electromagnetic radiation, each exposure comprising electromagnetic radiation at substantially one wavelengths from a number of wavelengths (step 210, FIG. 7a), at least some of the number of wavelengths substantially coinciding with wavelengths in an absorption spectrum of predetermined materials, at least some exposures from the number of exposures being at different wavelengths. At a number of pixels, and at each exposure, reflected/scattered electromagnetic radiation from the area of interest is detected (step 220, FIG. 7a). A number of pixelated images are obtained, one or more at each wavelength (steps 225, FIG. 7a). Illumination through the patterning component produces areas in each pixelated image that are not directly illuminated. For each one or more pixelated image, at each wavelength, one global pixelated image is obtained, the one global pixelated image being produced substantially by the areas not directly illuminated (step 227, FIG. 7a). A number of global pixelated images are processed (step 230, FIG. 17a). The number of global pixelated images, after processing, constitutes a vector of processed data at each pixel from a number of pixels. At each pixel, the vector of processed data is compared to a predetermined vector corresponding to a predetermined material (step 240, FIG. 7a), presence of the predetermined material being determined by the comparison.

Figure 7B:
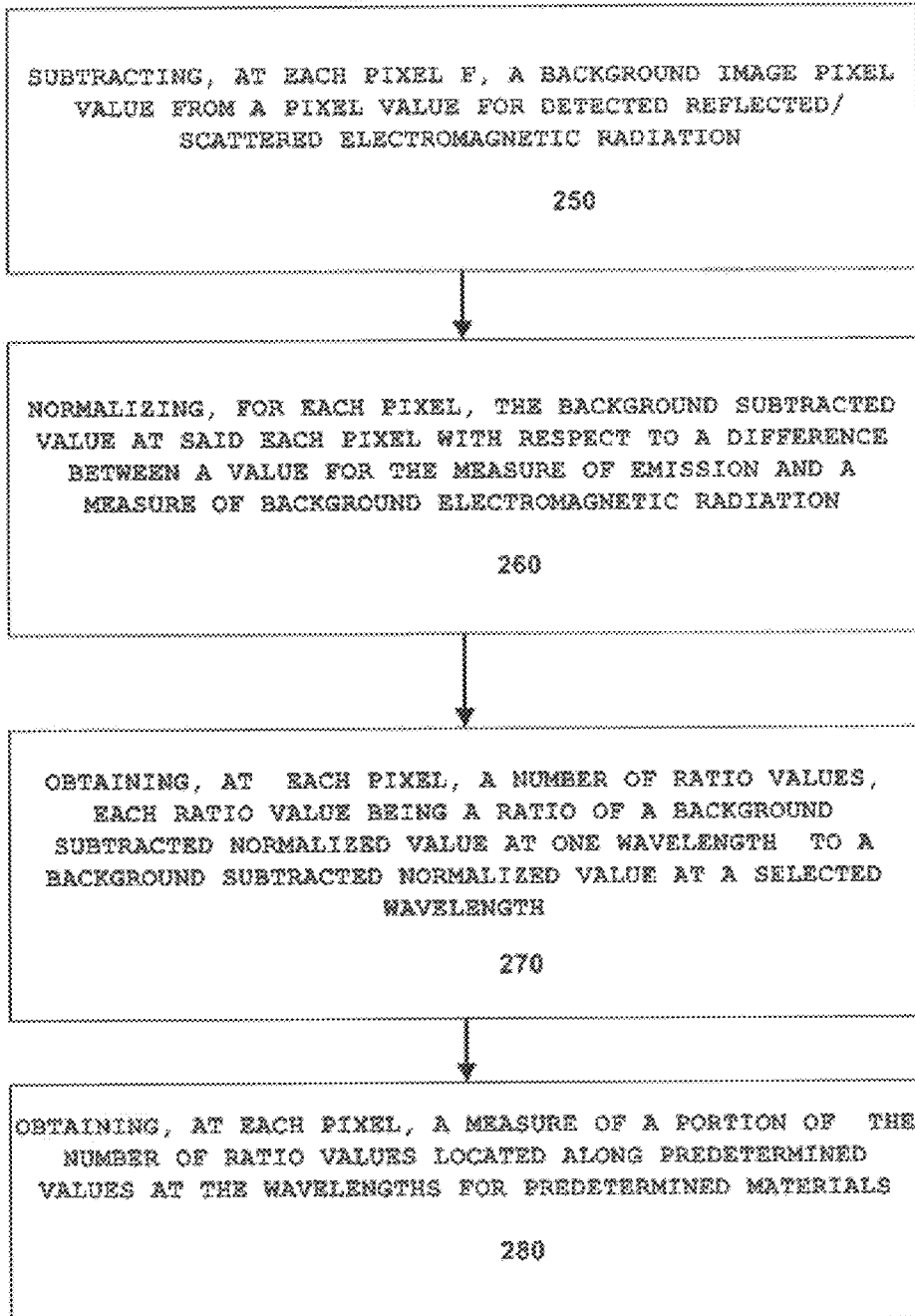

One embodiment of the processing and comparing steps is shown in FIG. 7b. In the embodiment shown in FIG. 7b, the processing and comparing steps include subtracting, at each pixel from the number of pixels, a background image pixel value from a pixel value for detected reflected/scattered electromagnetic radiation (step 250, FIG. 7b), the subtraction producing a background subtracted value at said each pixel. For each pixel, the background subtracted value at said each pixel is normalized with respect to a difference between a value for the measure of emission and a measure of background electromagnetic radiation (step 260, FIG. 7b). At each pixel, a number of ratio values are obtained (step 270, FIG. 7b), each ratio value being a ratio of a background subtracted normalized value at one wavelength from the number of wavelengths to a background subtracted normalized value at a selected wavelengths from the number of wavelengths. At said each pixel, a measure of a portion of the number of ratio values located along predetermined values at the number of wavelengths for predetermined materials is obtained (the measure is a result of the projection of the vector of processed data onto the predetermined vector corresponding to a predetermined material), a presence of the predetermined materials being ascertainable from that measure.

In one instance, the steps of sequentially illuminating and detecting are performed using a handheld device. In one embodiment, sequentially illuminating and detecting are performed while scanning the area of interest with the handheld device. In another embodiment, sequentially illuminating and detecting are performed in a point-and-shoot manner.

The following describes one exemplary embodiment of the data processing steps taken to generate differential or ratio images and finally a multidimensional vector that can be used to distinguish the presence of materials, explosives in one embodiment, based on their unique optical absorption patterns.

It should be noted that other embodiments are within the scope of these teachings.

Data Processing

Data processing is used to identify those areas of the images where wavelength specific attenuation has occurred due to the presence of an explosive. This processing treats the images as a 2-dimensional data array and operates on the individual pixel elements of the arrays that make up the images to generate new 2-D arrays. The new 2-D arrays can be transformed back into images by mapping the individual pixel values, in one instance, not a limitation of these teachings, over a 256 step grey scale according to the pixel's value.

Step 1 Background Subtraction

The first step in data processing involves subtraction of background ambient light. This step involves subtracting the pixel value in the background image from the corresponding pixel value in each of the laser illuminated images. The result is a new image array for each wavelength wherein the pixel values are proportional to only the laser light being reflected back to the camera.

Step 2 Normalization for Laser Launch Energy

The output power of the laser diodes is only moderately controlled. Rather than providing a strict control over the actual power launched we simply measure the launch power at the end of the combiner fiber optic then normalize each background corrected image for the launch level of the laser with which the image was collected. Normalization involves dividing each pixel of the background corrected array with the signal value collected from the system's reference photodetector. The result is a new array with the same number of pixels as the background corrected image, but with each element of the array normalized to the laser output power.

Step 3 Calculating Differential or Ratio Intensity Image Data

The presence of an explosive in the area under surveillance would result in differences in the image data collected with laser wavelengths that coincide with absorption bands versus those that do not. Two simple ways to see these differences is to generate differential or ratio images. A differential image can be generated by subtracting the pixel value for each pixel of one image from the corresponding pixel values of another image collected under illumination at a different wavelength. It is important that this operation be done on corresponding pixels in the two images as each pixel contains data on the reflected light intensity for one specific region of the image plane. Alternatively, a ratio image can be generated by calculating the quotient of the pixel values for each pixel of one image and the corresponding pixel values from a second image taken at a different wavelength.

Difference images constructed by subtracting background-subtracted and normalized image data collected at an absorbing wavelength from data collected at a non absorbing wavelength will appear whiter in any area where an explosive is present. This is due to the lower pixel values in that area of the image where the optically attenuating explosive exists.

Similarly, ratio images constructed by taking the quotient of background subtracted and normalized image data at an absorbing wavelength and data collected at a non absorbing wavelength will appear darker in those areas of the image where explosives are present.

Step 4 Vector Treatment and Analysis of Image Data

Differential or ratio images can be generated using any unique combination of wavelength images collected by the system. The individual pixel values within the multiple image data sets generated by these treatments can be used to produce a single vector representation of the complete set of images. The vector is calculated by treating each differential or ratio image as a dimension in an n-dimensional space wherein "n" is the total number of unique difference or ratio images. The projection of the vector along each dimension is defined by the value of a pixel within the differential or ratio image data set. For example, assume the system is using three (3) wavelengths so there are three (3) unique ratio image data sets (1/2, 1/3, and 2/3) containing N×M pixels each. A 3-dimensional vector representation of any pixel within the three arrays can be then generated by setting the projection along each orthogonal dimension equal to the value of the pixel in the respective array. In other words, if you just look at one pixel within the array and treat the ratio 1/2 as the x-axis in a 3-dimensional (m) space the value of X in our 3-dimensional space would be equal to that pixel's value in the 1/2 image data set. We could similarly set the value of the same pixel in the 1/3 image data set as the projection along the y-axis and the same pixel's value in the 2/3 image data set as the projection along the z-axis. The data for that pixel could then be defined as the vector—$(X_{1/2}, Y_{1/3}, Z_{2/3})$ wherein the magnitude of the vector is with respect to the origin. This same calculation can be run on every pixel in the image data sets for as many unique combinations of wavelengths as the user wishes. In some cases it is better to not use all the possible permutations, but only a select subset. The selection of an optimal set of combinations requires experimentation with the spectral characteristics of the explosives of interest and spectrum from different potential interfering agents.

The vector that is formed by the spectral results of differential or ratio imaging can then be used to determine if an unknown set of images contains any of the explosives of interest or not by comparing the pixel vectors (pixel-by-pixel). This process looks at the projection of the unknown image data vectors onto the known explosives vectors. This comparison can look at the direction and magnitude or just direction. The direction is relative to the known explosives vectors (angle between the two vectors). This is easily calculated using the expression:

$$\theta = \arccos\left(\frac{k \cdot u}{\|k\|\|u\|}\right),$$

where k·u is the dot product of the known explosive and unknown vectors and $\|v\|$ denotes the magnitude of the vectors (square root sum of the squares for all the dimensions). Note: previously we defined the "metric" as simply the value of $\cos(\theta)$. The result will only be zero (or nearly zero) when the two vectors have the same direction (i.e., the two vector are from the same type of material).

An alternative treatment of the image data is to digitize it by setting a threshold value above which the differential or ratio is set equal to 1 and below which it is set equal to 0. Differential or ratio image data sets can be analyzed in much the same way as the non digitized data sets.

In one embodiment of the system of these teachings, the system includes one or more processors and one or more computer usable media that has computer readable code embodied therein, the computer readable code causing the one or more processors to execute at least a portion of the method of these teachings. The one or more processors and the one or more computer usable media are operatively connected.

An electrical and software block diagram of the exemplary embodiment is shown in FIG. 8. Referring to FIG. 8, in the embodiment shown there in, a timing component 45, PIC triggering system, provides the timing initiation signal (trigger) to the electromagnetic radiation source 10, a laser system, to the detection system 50, an InGaAs camera, and to the analysis subsystem 55. The detection system 50 provides the data to the analysis subsystem 55 by means of an input component 110, a frame grabber card, which communicates with the analysis subsystem 55 by means of a frame grabber DLL. An image analysis library 115 provides, in one embodiment, the predetermined vector corresponding to a predetermined material to the analysis subsystem 55.

Step 5 Presenting Results

The vector comparison results can be presented as a grey scale image like the simpler differential or ratio image data or thresh holding can be applied to highlight those areas of the image where the angle between the vectors would indicate a reason for concern (i.e., presence of explosives identified). In the grey scale approach the absolute vector angular differences would be translated into a grey scale value wherein the grey scale values map the angular range of 0 and 180°. Setting the dark end of the grey scale equal to 0° would yield images with darker regions in the areas of the image where the vector differences were zero or nearly zero indicating the potential for the presence of explosives. Alternatively, a threshold comparison can be applied to the vector differences and only those pixels whose values are very close to zero assigned a value of 0 and all other pixels assigned a value of 1 (or vice versa). Images generated following this type of treatment would be sharply contrasted. Another, perhaps better way, to present the results would be to overlay the thresholded image results with a single image using red or a colored scale (blue to red) to highlight the values for the angular difference. The single image could be any one of the original images collected under a single wavelength illumination. The color scale could highlight in red those areas of greatest concern (very low or zero angular difference between the known and unknown vectors). One advantage to this approach is that the operator would see a full grey scaled image of the area under surveillance making it easier to identify the potential suspect or object holding the explosives.

In order to further better illustrate the present teachings, an exemplary embodiment of the data processing is disclosed hereinbelow.

The purpose of the process is to remove the ambient light effect and help to detect the materials, explosives in the exemplary embodiment. The example includes four (4) lasers from which three (3) ratio images are generated. A graphic showing how a vector is constructed in three-dimensional space from the projection of X, Y, and Z components is also provided. This graphic shows a simulated vector for an explosive (Ve) and a simulated vector for an unknown compound (Vu) having a sizeable angular difference between them.

Data Processing Method

1. Normalize the Laser Image with Photo Diode Reading

For each laser image, normalization is done using Equation 1, $$\alpha_i = \frac{L_i \; BK}{PIN_i - PIN_{BK}} \quad i = 1, \ldots, 6 \tag{1}$$

where $L_i$ is the laser image, BK is the background image, $PIN_i$ and $PIN_{BK}$ are photo diode reading for laser and background, respectively. Here background image is the image acquired when no laser diode is turned on. The purpose of background image is to remove the effect of ambient light.

A background image and the raw laser image for L1 and L3 are shown in FIG. 1.

As we can see from the figure, the brightness of image for L1 and image for L3 is different. The PIN normalization is to eliminate such difference.

In FIG. 1 two DNT pouches are concealed under the two layers of clothes, however, from each single laser image, we cannot detect the DNT pouches.

2 Get the Ratios

After normalization in 2.1, N normalized frames are averaged to get $\overline{\alpha}_i$. The ratio images are computed using Equation 2.

$$r_j = \frac{\overline{\alpha}_i}{\overline{\alpha}_k} \quad j = 1, \ldots, 4 \; i, k \in [1, \ldots, 6] \tag{2}$$

3 Find the Dynamic Ranges

For the ratios obtained in 2.1, the dynamic range is broad. To control the dynamic range to exclude outliers, we assume the ratio values are close to Gaussian distribution, which can be seen from the ratios's histogram as shown in FIG. 1. The mean $\overline{r}_j$ and standard deviation $\sigma_j$ of the ratio image are computed. Through our experiments, we choose $[\overline{r}_j - 1.5*\sigma_j, \overline{r}_j + 1.5*\sigma_j]$ as the dynamic range. The benefit is that this dynamic range is computed automatically from the ratio image itself and can adapt to the lighting changes, 4 Map the Ratios to Gray Scale Image With the dynamic range ready, we can map the ratios to gray scale image as the final output. The mapping is done using equation (3).

$$I = 255 * \frac{r_j - (\overline{r}_j - 1.5*\sigma_j)}{3*\sigma_j} \tag{3}$$

After the mapping, the ratio computed by equation (2) is mapped to a gray scale image and can be detected by human eyes. FIG. 2 shows some ratio images for the case when a human subject conceals the DNT pouch under two layers of clothes.

5 Vectors from Multiple Laser Ratio

To fuse the information from individual ratio, we propose to form a vector feature from multiple ratios, as shown in equation (4).

$$v = (r_i, r_j, r_k) i, j, k \in [1, \ldots, 4] \tag{4}$$

In such a way, the individual ratio becomes the component of the vector. Such a vector combines the information from multiple lasers and will have stronger detection capability than single ratio. An example vector given in equation (4) is shown in FIG. 1, where $V_e$ is the vector from explosive region and $V_u$ is from other regions. There is an angle $\theta$ between the two vectors.

The principle for the vector based detection is: each individual ratio will generate values different for regions with and without explosive pouches. Therefore, the vectors composed of these ratios in explosive region will point to some specified direction with certain magnitude, while vectors without explosive pouches will point to some uncertain directions and magnitude. In such way, the region with explosive pouches will be detected.

While the above exemplary embodiment referred to the detection of explosives, these teaching are not limited only to detecting explosives and the method can be applied to other concealed materials.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

The detection method of the present teachings is preferably performed at some finite distance from the material being detected, which is referred to as the "standoff distance", The standoff distance could be in the range of from 1 cm to 100 m. In all cases, the material being detected may be concealed under some type of covering materials such as cloth, paper, plastic, or leather that has substantial optical absorption and/or light scattering properties which obscures viewing the concealed material under the covering material with light in the visible wavelength range (400-700 nm).

Elements and components described herein may be further divided into additional components or joined together to form fewer components for performing the same functions.

The following is a disclosure by way of example of a device configured to execute functions (hereinafter referred to as computing device) which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least include a computing device. The computing device may include an inter-connect (e.g., bus and system core logic), which can interconnect such components of a computing device to a data processing device, such as a processor(s) or micropro-cessor(s), or other form of partly or completely programmable or pre-programmed device, e.g., hard wired and or application specific integrated circuit ("ASIC") customized logic circuitry, such as a controller or microcontroller, a digital signal processor, or any other form of device that can fetch instructions, operate on pre-loaded/pre-programmed instructions, and/or followed instructions found in hard-wired or customized circuitry to carry out logic operations that, together, perform steps of and whole processes and functionalities as described in the present disclosure.

Each computer program may be implemented in any programming language, such as assembly language, machine language, a high-level procedural programming language, or an object-oriented programming language. The programming language may be a compiled or interpreted programming language, Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

In this description, various functions, functionalities and/or operations may be described as being performed by or caused by software program code to simplify description. However, those skilled in the art will recognize what is meant by such expressions is that the functions result from execution of the program code/instructions by a computing device as described above, e.g., including a processor, such as a microprocessor, microcontroller, logic circuit or the like, Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metalization(s) interconnects of the base gate array ASIC architecture or selecting and providing metalization(s) interconnects between standard cell functional blocks included in a manufacturer's library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The interconnect may connect the data processing device to define logic circuitry including memory. The interconnect may be internal to the data processing device, such as coupling a microprocessor to on-board cache memory or external (to the microprocessor) memory such as main memory, or a disk drive or external to the computing device, such as a remote memory, a disc farm or other mass storage device, etc. Commercially available microprocessors, one or more of which could be a computing device or part of a computing device, include a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc, or a 68xxx series microprocessor from Motorola Corporation as examples.

The inter-connect in addition to interconnecting such as microprocessor(s) and memory may also interconnect, such elements to a display controller and display device, and/or to other peripheral devices such as input/output (I/O) devices, e.g., through an input/output controller(s). Typical I/O devices can include a mouse, a keyboard(s), a modem(s), a network interface(s), printers, scanners, video cameras and other devices which are well known in the art. The interconnect may include one or more buses connected to one another through various bridges, controllers and/or adapters. In one embodiment the I/O controller includes a USE (Universal Serial Bus) adapter for controlling USE peripherals, and/or an IEEE-1394 bus adapter for controlling IEEE-1394 peripherals.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile ROM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD RAM, a CD ROM, a DVD or a CD), or other type of memory system which maintains data even after power is removed from the system.

A server could be made up of one or more computing devices. Servers can be utilized, e.g., in a network to host a network database, compute necessary variables and information from information in the database(s), store and recover information from the database (s) track information and variables, provide interfaces for uploading and downloading information and variables, and/or sort or otherwise manipulate information and data from the database(s). In one embodiment a server can be used in conjunction with other computing devices positioned locally or remotely to perform certain calculations and other functions as may be mentioned in the present application, Common forms of computer-readable media include, for example, a floppy disk, a flexible disk, hard disk, magnetic tape, or any other magnetic medium, a CDROM, any other optical medium, any physical medium with patterns of holes, a RAM, a PROM, and EPROM, a FLASH-EPROM, any other memory chip or cartridge, all of which are non-transitory. As stated in the USPTO 2005 Interim Guidelines for Examination of Patent Applications for Patent Subject Matter Eligibility, 1300 Off, Gaz. Pat. Office 142 (Nov. 22, 2005), "On the other hand, from a technological standpoint, a signal encoded with functional descriptive material is similar to a computer-readable memory encoded with functional descriptive material, in that they both create a functional interrelationship with a computer. In other words, a computer is able to execute the encoded functions, regardless of whether the format is a disk or a signal."

Although these teachings have been described with respect to various embodiments, it should be realized these teachings is also capable of a wide variety of further and other embodiments within the spirit and scope of the claims.

What is claimed is:

1. A system comprising:
    at least one detecting component detecting incident electromagnetic radiation at a number of pixels;
    a number of electromagnetic radiation sources; each electromagnetic radiation source emitting at substantially one wavelengths from a number of wavelengths; at least some of the number of wavelengths substantially coinciding with wavelengths in an absorption spectrum of predetermined materials; the number of electromagnetic radiation sources emitting substantially from one location; the at least one detecting component receiving reflected/scattered electromagnetic radiation from an area of interest;
    a patterning component disposed between the number of electromagnetic radiation sources and the area of interest; the patterning component receiving electromagnetic radiation from at least one electromagnetic radiation source from the number of electromagnetic radiation sources and providing at least a portion of the electromagnetic radiation received to the area of interest; each one of the number of the electromagnetic radiation sources sequentially illuminating the patterning component;
    a modulating component modulating, with respect to time, emission from said each one of the number of electromagnetic radiation sources; and
    an analysis component configured to:
        obtain a number of pixelated images by sequentially illuminating the area of interest; illumination through the patterning component producing areas in each pixelated image that are not directly illuminated;
        obtain, for each one or more pixelated images from the number of pixelated images, the one or more pixelated images illuminated at substantially one wavelength, one pixelated image, labeled a global pixelated image, produced substantially by the areas are not directly illuminated, constituting a number of global pixelated images;
        process the number of global pixelated images; the number of global pixelated images, after processing, constituting a vector of processed data at each pixel from a number of pixels; and
        compare, at each pixel, the vector of processed data to a predetermined vector corresponding to a predetermined material;
        presence of the predetermined material being determined by comparing.

2. The system of claim 1 wherein the analysis component comprises:
    a background subtraction subcomponent configured for subtracting, at each pixel from the number of pixels, a background image pixel value from a pixel value for detected reflected/scattered electromagnetic radiation; the background subtraction subcomponent producing a background subtracted value at said each pixel;
    a ratio intensity subcomponent configured for obtaining, at said each pixel, a number of ratio values, each ratio value being a ratio of a background subtracted value at one wavelength from the number of wavelengths to a background subtracted value at a selected wavelengths from the number of wavelengths; and
    a projection subcomponent configured for obtaining, at said each pixel, a measure of a portion of the number of ratio values located along predetermined values at the number of wavelengths for said predetermined materials;
    a presence of said predetermined materials being ascertainable from said measure.

3. The system of claim 2 wherein the analysis component further comprises a normalizing component configured to normalize, for said each pixel, the background subtracted value at said each pixel respect to a difference between a value for a measure of emission from one of the number of electromagnetic radiation sources and a measure of background electromagnetic radiation.

4. The system of claim 2 wherein emission substantially from one location for the number of electromagnetic radiation sources is provided by use of an optical subsystem.

5. The system of claim 4 wherein the optical subsystem comprises fiber optic pigtails optically coupled to each electromagnetic radiation source from the number of electromagnetic radiation sources; and an optical combiner receiving radiation from the fiber optic pigtails.

6. The system of claim 5 wherein the optical subsystem comprises a number of dichroic beam splitters, each dichroic beam splitter receiving electromagnetic radiation from one or more of the number of electromagnetic radiation sources; and an optical fiber receiving electromagnetic radiation from the number of dichroic beam splitters.

7. The system of claim 2 wherein said analysis component comprises:
    at least one processor; and
    at least one computer usable medium having computer readable code embodied therein, the computer readable code causing said at least one processor to:
        subtract, at each pixel from the number of pixels, a background image pixel value from a pixel value for detected reflected/scattered electromagnetic radiation;
        subtraction producing a background subtracted value at said each pixel;
        obtain, at said each pixel, a number of ratio values, each ratio value being a ratio of a background subtracted value at one wavelength from the number of wavelengths to a background subtracted value at a selected wavelength from the number of wavelengths; and obtain, at said each pixel, a measure of a portion of the number of ratio values located along predetermined values at the number of wavelengths for said predetermined materials;

said at least one processor and said at least one computer usable medium constituting the background subtraction subcomponent, the ratio intensity subcomponent and the projection subcomponent.

8. The system of claim 7 wherein the computer readable code further causes said at least one processor to:

normalize, for said each pixel, the background subtracted value at said each pixel with respect to a difference between a value for a measure of emission from one of the number of electromagnetic radiation sources and a measure of background electromagnetic radiation.

9. The system of claim 1 further comprising a timing component providing a signal for initiation of emission from a selected one of the number of electromagnetic radiation sources; the timing component also providing said initiation signal for initiating detection by the detecting component.

10. The system of claim 9 further comprising an electromagnetic emission monitoring component; wherein the timing component provides said initiation signal for initiating monitoring of electromagnetic emission from the selected one of the number of electromagnetic radiation sources.

11. The system of claim 1 wherein said analysis component, in being configured to obtain, for said each one pixelated image from the number of pixelated images, said one global pixelated image, is configured to:

obtain at least two detected images; and obtain said one global pixelated image from the at least two detected images.

12. The system of claim 11 wherein the at least two detected images comprise two images; and wherein said two images comprise two complementary images.

13. The system of claim 1 wherein said analysis component, in being configured to obtain, for said each one pixelated image from the number of pixelated images, said one global pixelated image, is configured to:

obtain one high-resolution pixelated image at a resolution of a predetermined number of times a predetermined resolution of said one pixelated image;

label each pixel as a maximum or a minimum if a brightness of said each pixel is maximum or minimum in a predetermined window around said each pixel;

interpolate to obtain one maximum image of the predetermined resolution, the one maximum image obtained from interpolation of pixels labeled as maximum, and one minimum image of the predetermined resolution, the one minimum image obtained from interpolation of pixels labeled as minimum; and obtain said one global pixelated image from the one maximum image and the one minimum image.

14. A method for detecting concealed objects, the method comprising:

sequentially illuminating, for a number of exposures, through a patterning component, an area of interest with electromagnetic radiation; each exposure comprising electromagnetic radiation at substantially one wavelengths from a number of wavelengths; the electromagnetic radiation being modulated with respect to time; at least some of the number of wavelengths substantially coinciding with wavelengths in an absorption spectrum of predetermined materials; at least some exposures from the number of exposures being at different wavelengths;

detecting, at a number of pixels, and at each exposure, reflected/scattered electromagnetic radiation from the area of interest; the reflected/scattered electromagnetic radiation from the area of interest being detected by one or more detecting components; obtaining a number of pixelated images from the one or more detecting components; illumination through their patterning component producing areas in each pixelated image that are not directly illuminated;

obtaining, for each one or more pixelated images from the number of pixelated images, the one or more pixelated images illuminated at substantially one wavelength, one pixelated image, labeled a global pixelated image, produced substantially by the areas are not directly illuminated; constituting a number of global pixelated images;

processing the number of global pixelated images; the number of global pixelated images, after processing, constituting a vector of processed data at each pixel from a number of pixels; and comparing, at each pixel, the vector of processed data to a predetermined vector corresponding to a predetermined material;

presence of the predetermined material being determined by said comparing.

15. The method of claim 14 wherein processing and comparing comprise:

subtracting, at each pixel from the number of pixels, a background image pixel value from a pixel value for detected reflected/scattered electromagnetic radiation; the subtraction producing a background subtracted value at said each pixel;

obtaining, at said each pixel, a number of ratio values, each ratio value being a ratio of a background subtracted value at one wavelength from the number of wavelengths to a background subtracted value at a selected wavelengths from the number of wavelengths;

obtaining, at said each pixel, a measure of a portion of the number of ratio values located along predetermined values at the number of wavelengths for predetermined materials; a presence of said predetermined materials being ascertainable from said measure.

16. The method of claim 15 further comprising:

monitoring emission for each exposure; the monitoring providing a measure of emission for said each exposure; and normalizing, for said each pixel, the background subtracted value at said each pixel with respect to a difference between a value for the measure of emission and a measure of background electromagnetic radiation.

* * * * *

UNITED STATES PATENT AND TRADEMARK OFFICE
CERTIFICATE OF CORRECTION

PATENT NO.        : 9,491,378 B2
APPLICATION NO.   : 14/246606
DATED             : November 8, 2016
INVENTOR(S)       : James A. Kane et al.

Page 1 of 1

It is certified that error appears in the above-identified patent and that said Letters Patent is hereby corrected as shown below:

In the Claims

In Column 21, Line 30 (Claim 1), "one wavelengths from a number of wavelengths;" should read -- one wavelength from a number of wavelengths; --

In Column 22, Lines 19-20 (Claim 2), "a selected wavelengths from the number of wavelengths;" should read -- a selected wavelength from the number of wavelengths; --

In Column 22, Line 31 (Claim 3), "at said each pixel respect" should read -- at said each pixel with respect --

In Column 23, Line 59 - Column 24, Line 1 (Claim 14), "one wavelengths from a number of wavelengths;" should read -- one wavelength from a number of wavelengths; --

In Column 24, Lines 43-44 (Claim 15), "a selected wavelengths from the number of wavelengths;" should read -- a selected wavelength from the number of wavelengths; --

Signed and Sealed this
Fourteenth Day of February, 2017

Michelle K. Lee
*Director of the United States Patent and Trademark Office*